US011395622B2

(12) United States Patent
Linders et al.

(10) Patent No.: US 11,395,622 B2
(45) Date of Patent: Jul. 26, 2022

(54) FOOTWEAR SYSTEM FOR ULCER OR PRE-ULCER DETECTION

(71) Applicant: Podimetrics, Inc., Somerville, MA (US)

(72) Inventors: David R. Linders, Waltham, MA (US); Brian J. Petersen, Somerville, MA (US); Daniel J. Petersen, Medford, MA (US); Jonathan D. Bloom, Medford, MA (US)

(73) Assignee: Podimetrics, Inc., Somerville, MA (US)

( * ) Notice: Subject to any disclaimer, the term of this patent is extended or adjusted under 35 U.S.C. 154(b) by 94 days.

(21) Appl. No.: 15/343,892

(22) Filed: Nov. 4, 2016

(65) Prior Publication Data
US 2017/0127999 A1 May 11, 2017

Related U.S. Application Data

(60) Provisional application No. 62/251,879, filed on Nov. 6, 2015.

(51) Int. Cl.
*A61B 5/00* (2006.01)
*G16H 40/63* (2018.01)
(Continued)

(52) U.S. Cl.
CPC ............... *A61B 5/445* (2013.01); *A43B 3/34* (2022.01); *A43B 7/00* (2013.01); *A61B 5/0002* (2013.01);
(Continued)

(58) Field of Classification Search
CPC ......... A61B 5/00–5/7495; A61B 5/445; A61B 5/447; A61B 5/015; A61B 5/7282; A61B 5/6807; A61B 2505/07
See application file for complete search history.

(56) References Cited

U.S. PATENT DOCUMENTS

| 4,374,384 A | 2/1983 | Moates |
| 4,574,359 A | 3/1986 | Ishizaka et al. ............. 364/557 |

(Continued)

FOREIGN PATENT DOCUMENTS

| CN | 1308225 | 8/2001 | ............. G01K 3/00 |
| CN | 201312800 | 9/2009 | ............. A61B 5/00 |

(Continued)

OTHER PUBLICATIONS

Ammer et al., *Thermal Imaging of Skin Changes on the Feet of Type II Diabetics*, 2001 Conference Proceedings of the 23$^{rd}$ Annual International Conference of the IEEE Engineering in Medicine and Biology Society, Istanbul, Turkey, Oct. 25-28, 2001, 4 pages.

(Continued)

*Primary Examiner* — Daniel L Cerioni
*Assistant Examiner* — Raymond P Dulman
(74) *Attorney, Agent, or Firm* — Nutter McClennen & Fish LLP

(57) ABSTRACT

A footwear system having a plurality of temperature sensors determines the emergence of an ulcer or pre-ulcer on a person's foot. After the plurality of temperature sensors generate a plurality of discrete temperature data values, the system and method form a temperature map representing substantially the actual geometric shape of at least a portion of the foot, and the distribution of temperatures of the at least a portion of the foot. Next, the method and system determine whether the temperature map presents at least one of a plurality of prescribed patterns, and produces output information indicating an emergence of an ulcer or a pre-ulcer on a given portion on the foot. The output information is produced as a function of whether the temperature map is determined to present the at least one of the plurality of prescribed patterns.

28 Claims, 15 Drawing Sheets

(51) Int. Cl.
    *G16H 50/20*         (2018.01)
    *G01K 1/02*          (2021.01)
    *G01K 1/00*          (2006.01)
    *A43B 7/00*          (2006.01)
    *G01K 13/20*        (2021.01)
    *A43B 3/34*          (2022.01)
    *A61B 5/01*          (2006.01)

(52) U.S. Cl.
    CPC .............. *A61B 5/015* (2013.01); *A61B 5/447* (2013.01); *A61B 5/6807* (2013.01); *A61B 5/7282* (2013.01); *A61B 5/742* (2013.01); *A61B 5/7405* (2013.01); *G01K 1/00* (2013.01); *G01K 1/026* (2013.01); *G01K 13/20* (2021.01); *G16H 40/63* (2018.01); *G16H 50/20* (2018.01); *A61B 2505/07* (2013.01); *G01K 2213/00* (2013.01)

(56) References Cited

U.S. PATENT DOCUMENTS

| | | | |
|---|---|---|---|
| 4,592,000 A | 5/1986 | Ishizaka et al. | 364/557 |
| 4,629,336 A | 12/1986 | Ishizaka | 374/169 |
| 4,647,918 A | 3/1987 | Goforth | 340/573 |
| 4,648,055 A | 3/1987 | Ishizaka et al. | 164/557 |
| 4,843,577 A | 6/1989 | Muramoto | 364/557 |
| 4,849,885 A | 7/1989 | Stillwagon et al. | |
| 4,866,621 A | 9/1989 | Ono | 364/413.03 |
| 4,878,184 A | 10/1989 | Okada et al. | 364/557 |
| 5,011,294 A | 4/1991 | Yamaguchi | 374/107 |
| 5,015,102 A | 5/1991 | Yamaguchi | 374/107 |
| 5,066,141 A | 11/1991 | Ikeda et al. | 374/169 |
| 5,259,389 A | 11/1993 | Muramoto et al. | 128/736 |
| 5,473,629 A | 12/1995 | Muramoto | 374/102 |
| 5,642,096 A | 6/1997 | Leyerer et al. | 340/573 |
| 5,678,566 A | 10/1997 | Dribbon | 128/779 |
| 5,929,332 A | 7/1999 | Brown | 73/172 |
| 6,077,228 A | 6/2000 | Schonberger | |
| 6,090,050 A | 7/2000 | Constantinides | 600/549 |
| 6,195,921 B1 | 3/2001 | Truong | 36/136 |
| 6,398,740 B1 | 6/2002 | Lavery et al. | 600/549 |
| 6,631,287 B2 | 10/2003 | Newman et al. | 600/474 |
| 6,767,330 B2 | 7/2004 | Lavery et al. | 600/549 |
| 6,807,869 B2 | 10/2004 | Farringdon et al. | 73/862.046 |
| 6,963,772 B2 | 11/2005 | Bloom et al. | 600/547 |
| 7,052,472 B1 | 5/2006 | Miller et al. | 600/549 |
| 7,167,734 B2 | 1/2007 | Khalil et al. | 600/310 |
| 7,206,718 B2 | 4/2007 | Cavanagh et al. | 702/155 |
| 7,318,004 B2 | 1/2008 | Butterfield | 702/130 |
| 7,563,024 B2 | 7/2009 | Rotem et al. | |
| 7,637,657 B2 | 12/2009 | Yamamoto et al. | 374/169 |
| 7,716,005 B2 | 5/2010 | Shoureshi et al. | 702/131 |
| 7,726,206 B2 * | 6/2010 | Terrafranca, Jr. | A43B 13/00 73/862.041 |
| 7,758,523 B2 | 7/2010 | Collings et al. | 600/592 |
| 8,360,987 B2 | 1/2013 | Kantro et al. | 600/549 |
| 8,454,539 B2 | 6/2013 | Vuillerme et al. | |
| 9,095,305 B2 | 8/2015 | Engler et al. | 600/587 |
| 9,259,178 B2 | 2/2016 | Bloom et al. | 600/587 |
| 9,271,672 B2 | 3/2016 | Linders et al. | 600/549 |
| 9,326,723 B2 | 5/2016 | Petersen et al. | A61B 5/447 |
| 2002/0082486 A1 | 6/2002 | Lavery et al. | 600/300 |
| 2002/0143257 A1 | 10/2002 | Newman et al. | |
| 2005/0165284 A1 | 7/2005 | Gefen | |
| 2006/0021261 A1 | 2/2006 | Face | 36/132 |
| 2006/0030783 A1 | 2/2006 | Tsai et al. | 600/547 |
| 2007/0038273 A1 | 2/2007 | Bales et al. | 607/88 |
| 2007/0039211 A1 | 2/2007 | Pichler | 36/140 |
| 2007/0043408 A1 | 2/2007 | Winnett et al. | 607/96 |
| 2008/0214962 A1 | 9/2008 | Kantro et al. | 600/592 |
| 2008/0238660 A1 | 10/2008 | Dayton et al. | |
| 2009/0143843 A1 | 6/2009 | Bales et al. | |
| 2009/0219972 A1 | 9/2009 | Carlsson et al. | 374/137 |
| 2009/0306801 A1 | 12/2009 | Sivak et al. | 700/98 |
| 2010/0004566 A1 | 1/2010 | Son et al. | 600/592 |
| 2010/0041998 A1 | 2/2010 | Postel | 600/475 |
| 2010/0063778 A1* | 3/2010 | Schrock | A61B 5/1038 702/188 |
| 2010/0198022 A1 | 8/2010 | Vuillerme et al. | 600/301 |
| 2010/0268111 A1 | 10/2010 | Drinan et al. | 600/547 |
| 2010/0324455 A1 | 12/2010 | Rangel et al. | 600/592 |
| 2011/0015498 A1 | 1/2011 | Mestrovic et al. | 600/301 |
| 2011/0054359 A1* | 3/2011 | Sazonov | A61B 5/4866 600/595 |
| 2011/0214501 A1 | 9/2011 | Ross et al. | 73/172 |
| 2011/0263950 A1* | 10/2011 | Larson | A61B 5/02055 600/301 |
| 2011/0275956 A1 | 11/2011 | Son et al. | 600/592 |
| 2011/0313314 A1 | 12/2011 | Gefen | 600/555 |
| 2012/0109013 A1* | 5/2012 | Everett | A61B 5/1038 600/587 |
| 2012/0190989 A1 | 7/2012 | Kaiser et al. | 600/476 |
| 2012/0221286 A1 | 8/2012 | Bisch et al. | 702/131 |
| 2013/0019503 A1 | 1/2013 | Vogt | 36/103 |
| 2013/0162796 A1 | 6/2013 | Bharara et al. | |
| 2013/0211281 A1 | 8/2013 | Ross et al. | 600/549 |
| 2013/0261494 A1* | 10/2013 | Bloom | A61B 5/447 600/549 |
| 2013/0261496 A1 | 10/2013 | Engler et al. | |
| 2015/0057562 A1 | 2/2015 | Linders et al. | 600/549 |
| 2017/0188841 A1 | 7/2017 | Ma et al. | |
| 2018/0132730 A1 | 5/2018 | Linders et al. | |
| 2018/0249945 A1* | 9/2018 | Najafi | A61B 5/112 |

FOREIGN PATENT DOCUMENTS

| | | | |
|---|---|---|---|
| CN | 202263087 | 6/2012 | ............ A61F 7/00 |
| DE | 202010013176 U1 | 3/2011 | ............ A43B 7/14 |
| DE | 20 2014 105 408 U1 | 11/2014 | ............ A61B 5/00 |
| EP | 0 885 587 | 12/1998 | ............ A61B 5/00 |
| EP | 1511419 B1 | 8/2008 | ............ A61B 5/103 |
| JP | 55-071919 | 5/1980 | ............ G01K 1/02 |
| JP | H03-275039 A | 12/1991 | ............ A61B 5/00 |
| JP | 2002-269231 A | 9/2002 | ............ G06F 17/60 |
| JP | 2004-528085 A | 9/2004 | ............ A61B 5/00 |
| JP | 2005-533543 A | 11/2005 | ............ A61B 10/00 |
| JP | 2009-539454 | 11/2009 | ............ A61B 5/00 |
| KR | 101027367 | 4/2011 | ............ A61B 5/145 |
| KR | 10-2012-0007154 A | 1/2012 | |
| RU | 2433783 | 11/2011 | ............ A61B 5/01 |
| WO | 01/89367 A2 | 11/2001 | |
| WO | WO 2007/114768 | 10/2007 | ............ G01K 11/12 |
| WO | WO 2008/058051 | 5/2008 | ............ G01K 13/00 |
| WO | WO 2009/005373 | 1/2009 | ............ A61B 5/01 |
| WO | WO 2010/021932 | 2/2010 | ............ A61B 5/00 |
| WO | 2010/085163 A1 | 7/2010 | |
| WO | WO 2012/051394 | 4/2012 | ............ G01N 21/00 |
| WO | WO 2012/084814 | 6/2012 | ............ A43B 7/14 |
| WO | 2013/114291 A1 | 8/2013 | |
| WO | WO-2015/143218 | 9/2015 | |

OTHER PUBLICATIONS

Armstrong et al., *Monitoring Healing of Acute Charcot's Arthropathy with Infrared Dermal Thermometry*, Journal of Rehabilitation Research and Development, vol. 34, No. 3, pp. 317-321, Jul. 1997.

Frykberg et al., *Feasibility and Efficacy of a Smart Mat Technology to Predict Development of Diabetic Plantar Ulcers*, Diabetes Care, vol. 40, pp. 973-980, Jul. 2017.

European Patent Office, Notice of Opposition to a European Patent—European Patent No. 2833783B1, dated May 31, 2018, 8 pages.

International Searching Authority, International Search Report—International Application No. PCT/US2016/06038, dated Mar. 2, 2017, together with the Written Opinion of the International Searching Authority, 12 pages.

Bharara et al., "Coming events cast their shadows before: detecting inflammation in the acute diabetic foot and the foot in remission," Diabetes/Metabolism Research and Reviews, vol. 28, pp. 15-20, 2012.

Bharara, M, Bharara, M—PI—Technology Summary, 5 pages, undated.

(56) References Cited

OTHER PUBLICATIONS

Bloom, Declaration of Jonathan D. Bloom under 37 CFR §1.56, pp. 1-3, Feb. 28, 2016.
Brioschi et al., "Automated Computer Diagnosis of IR Medical Imaging," FLIR Technical Series, Application Note for Research & Science, FLIR Systems, Inc., 2011.
Caselli, M.D. et al., "The Forefoot-to-Rearfoot Plantar Pressure Ratio Is Increased in Severe Diabetic Neuropathy and Can Predict Foot Ulceration," Diabetes Care, vol. 25, No. 6, pp. 1066-1071, Jun. 2002.
Chen et al., "Development of a Thermal and Hyperspectral Imaging System for Wound Characterization and Metabolic Correlation," John Hopkins Apl Technical Digest, vol. 26, No. 1, pp. 67-74, 2005.
Dabiri et al., "Electronic Orthotics Shoe: Preventing Ulceration in Diabetics Patients," 30$^{th}$ Annual International IEEE EMBS Conference, pp. 771-774, Aug. 2008.
Engler, "Rock Health Presentation" of Aug. 24, 2012, 19 pages.
Engler, et al., Description of Public Disclosures reported in Medcitynews.com and CloudTop Articles along with Exhibits A-D, 32 pages, Sep. 2015.
Engler, Declaration of Jeffrey M. Engler under 37 CFR §1.56, 2 pages, Feb. 28, 2016.
Kaabouch et al., "Predicting neuropathic ulceration: analysis of static temperature distributions in thermal images," Journal of biomedical Optics, vol. 15, Sec. 6, pp. 061715-1-061715-6, 2010.
Liu et al., "Infrared Dermal Thermography on Diabetic Feet Soles to Predict Ulcerations: a Case Study," Proc. of SPIE, vol. 8572, pp. 85720N-1-85720N-9, 2013.
Liu et al., "Statistical analysis of spectral data: a methodology for designing an intelligent monitoring system for the diabetic foot," Predicting neuropathic ulceration: analysis of static temperature distributions in thermal images, Journal of Biomedical Optics, vol. 18(12), pp. 126004-1-126004-11, Dec. 2013.
Medgadget.com, "TempTouch for Foot Ulcer Detection," Xilas, Inc., 2 pages, Apr. 19, 2005.
Morley et al., "In-Shoe Multisensory Data Acquisition System," IEEE Transactions on Biomedical Engineering, vol. 48, No. 7, pp. 815-820, Jul. 2001.
Roback, "An overview of temperature monitoring devices for early detection of diabetic foot disorders," Linkoping University Post Print, 18 pages, 2010.
Siren Care, "Siren Care—Best Diabetic Socks Tracking Your Foot Health", https://siren.care/how-it-works , 4 pages, Jan. 6, 2017.
Van Netten et al., "Infrared Thermal Imaging for Automated Detection of Diabetic Foot Complications," Journal of Diabetes Science and Technology, vol. 7, Issue 5, pp. 1122-1129, Sep. 2013.
Visual Footcare Technologies, LLC, "TempStat," Visual Footcare Technologies, LLC, Thermal Imagine Device, One unit: $125, 1 page, undated.
Korean Intellectual Property Office, International Search Report—International Application No. PCT/US2013/030997, dated Jul. 8, 2013, together with the Written Opinion of the International Searching Authority, 13 pages.
European Patent Office, Supplementary European Search Report—Application No. EP 13 77 2800, dated Jun. 26, 2015, 7 pages.
Liu et al., "Automatic detection of diabetic foot complications with infrared thermography by asymmetric analysis," Journal of Biomedical Optics, 20(2), 11 pages (2015).
Supplementary European Search Report for European Patent Application No. 16863080, dated Apr. 30, 2019 (12 pages).

\* cited by examiner

FOOTWEAR SYSTEM FOR ULCER OR PRE-ULCER DETECTION

PRIORITY

This patent application claims priority from provisional U.S. patent application No. 62/251,879, filed Nov. 6, 2015, entitled, "WEARABLE SYSTEM FOR THE MEASUREMENT OF FOOT TEMPERATURE,", and naming David Robert Linders, Brian Jude Petersen, Daniel Joseph Petersen, and Jonathan David Bloom as inventors, the disclosure of which is incorporated herein, in its entirety, by reference.

RELATED APPLICATIONS AND PATENTS

This patent application is related to the following patents and patent applications, the disclosures of which are incorporated herein, in their entireties, by reference:
1. U.S. Pat. No. 9,259,178,
2. U.S. Pat. No. 9,095,305,
3. U.S. Pat. No. 9,271,672,
4. U.S. Pat. No. 9,326,723,
5. U.S. patent application Ser. No. 14/468,909, filed Aug. 26, 2014, entitled, "APPARATUS FOR MEASURING TEMPERATURE DISTRIBUTION ACROSS THE SOLE OF THE FOOT,", and naming David Robert Linders and Brian Petersen as inventors.
6. U.S. patent application Ser. No. 15/056,611, filed on Feb. 29, 2016, entitled, "METHOD AND APPARATUS FOR INDICATING THE EMERGENCE OF AN ULCER,", and naming David Robert Linders, Jonathan David Bloom, Jeffrey Mark Engler, Brian Jude Petersen, Adam Geboff, and David Charles Kale and as inventors,
7. U.S. patent application Ser. No. 15/144,658, filed on May 2, 2006, entitled, "METHOD AND APPARATUS FOR MONITORING FOOT IMFLAMMATION,", and naming Brian Petersen, Jonathan David Bloom, David Robert Linders, and Jeffrey Mark Engler as inventors.

FIELD OF THE INVENTION

The invention generally relates to footwear and, more particularly, the invention relates to footwear with temperature sensors for enhanced functionality.

BACKGROUND OF THE INVENTION

Open sores on an external surface of the body often form septic breeding grounds for infection, which can lead to serious health complications. For example, foot ulcers on the bottom of a diabetic's foot can lead to gangrene, leg amputation, or, in extreme cases, death. The healthcare establishment therefore recommends monitoring a diabetic's foot on a regular basis to avoid these and other dangerous consequences. Unfortunately, known techniques for monitoring foot ulcers, among other types of ulcers, often are inconvenient to use, unreliable, or inaccurate, thus reducing compliance by the very patient populations that need it the most.

SUMMARY OF VARIOUS EMBODIMENTS

In accordance with one embodiment of the invention, a footwear system has a body with both an interior for receiving a person's foot and opening to the interior, a flexible surface configured to at least in part conform to the person's foot, and a plurality of temperature sensors within the interior of the body. The plurality of temperature sensors are configured to generate a plurality of discrete temperature data values across the geometry of the foot. The footwear system also has temperature map generator, operatively coupled with the plurality of temperature sensors, configured to form a temperature map from the plurality of discrete temperature data values. The temperature map represents substantially the actual geometric shape of at least a portion of the foot, and includes the distribution of temperatures of the at least a portion of the foot.

To detect one or more ulcers or pre-ulcers, the footwear system has a pattern recognition system operably coupled with the temperature map generator. The pattern recognition system is configured to determine whether the temperature map presents at least one of a plurality of prescribed patterns. Those patterns may be determined from data relating to the foot itself and/or another foot. The pattern recognition system is operatively coupled with an analyzer configured to produce output information indicating an emergence of an ulcer or a pre-ulcer on a portion on the foot. To that end, the analyzer is configured to produce the output information as a function of whether the temperature map is determined to present the at least one of the plurality of prescribed patterns.

At least one of the temperature map generator, pattern recognition system and analyzer may be remote from the body. Accordingly, the footwear system also may have an interface to communicate with one or remote devices. In that case, the temperature sensors communicate with the at least one of the temperature map generator, pattern recognition system and analyzer using the interface. Alternatively, at least one of the temperature map generator, pattern recognition system and analyzer are integrated into the body of the footwear.

The temperature map generator preferably is configured to form a geometrically accurate outline of at least a portion of the foot based on the plurality of discrete temperature data values. Thus, using the temperature map, the analyzer may determine a region of the foot that presents at least one of the plurality of patterns. More specifically, the temperature map may be configured to form a geometric shape reflecting substantially the actual geometric shape of at least a portion of the foot of the person based on the plurality of discrete temperature data values ("foot geometry"). The temperature map thus may be configured to generate the distribution of temperatures over at least a part of the foot geometry, which the analyzer uses to determine whether the region presents the plurality of patterns.

Among other things, the temperature map may include a two dimensional representation of the sole of the foot and a plurality of the discrete temperature data values across the two dimensional representation. Alternatively, the temperature map may include, in addition to the noted two dimensional representation of the sole of the foot, a thermogram for the distribution of temperatures. Unlike the discrete temperature values, the thermogram includes a spatially continuous data set of two-dimensional temperature values across at least the at least a portion of the foot.

The footwear system may be implemented as a variety of modalities, such as a sock, shoe, boot, orthotic, sneaker, slipper and/or insole. Thus, the body may include a sock body, a shoe body, a sneaker body, and/or a slipper body. In addition or alternatively, the insole may be part of the body, or a separate part of the body. Moreover, the insole may at least in part support the plurality of temperature sensors.

In accordance with another embodiment, a method of determining the emergence of an ulcer or pre-ulcer on a foot of a person provides one or more processors and footwear having a flexible surface for receiving a foot of the person. To detect foot temperatures, the footwear has a plurality of temperature sensors. The method positions the foot inside the footwear so that at least a portion of the flexible surface flexes in response to receipt of the foot. The method generates, using the plurality of temperature sensors, a plurality of discrete temperature data values after receipt of the foot by the footwear, and then forms, by at least one of the processors from the discrete temperature data values, a temperature map representing substantially the actual geometric shape of at least a portion of the foot. The temperature map also includes the distribution of temperatures of the at least a portion of the foot. Next, the method determines, by at least one of the one or more processors, whether the temperature map presents at least one of a plurality of prescribed patterns, and produces, by at least one of the one or more processors, output information indicating an emergence of an ulcer or a pre-ulcer on a portion on the foot. The method produces the output information as a function of whether the temperature map is determined to present the at least one of the plurality of prescribed patterns.

In accordance with still other embodiments, a footwear system includes an insole for receiving a person's foot having an actual geometric shape. Specifically, the insole is configured to be positioned within the interior of a closed platform. The system also has plurality of temperature sensors in communication with a top surface of the insole. The plurality of temperature sensors are configured to generate a plurality of discrete temperature data values across the geometry of the foot. A temperature map generator operatively coupled with the plurality of temperature sensors is configured to form a temperature map from the plurality of discrete temperature data values. The temperature map represents substantially the actual geometric shape of at least a portion of the foot, and includes a distribution of temperatures of the at least a portion of the foot. The system further includes a pattern recognition system to determine whether the temperature map presents at least one of a plurality of prescribed patterns, and an analyzer configured to produce output information indicating an emergence of an ulcer or a pre-ulcer on a portion on the foot. The analyzer is configured to produce the output information as a function of whether the temperature map is determined to present the at least one of the plurality of prescribed patterns.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

Illustrative embodiments add intelligence to footwear to warn users of emerging foot ulcers and foot pre-ulcers. To that end, the footwear has a plurality of temperature sensors that cooperate with a map generator to produce a temperature map representing both the actual geometric shape and size of a person's foot (e.g., the sole of the foot), and the distribution of temperatures across the foot. Accordingly, because the temperature map is generally anatomically accurate, illustrative embodiments may more precisely locate hotspots that identify emerging foot ulcers and/or foot pre-ulcers. Details of illustrative embodiments are discussed below.

Figure 1:
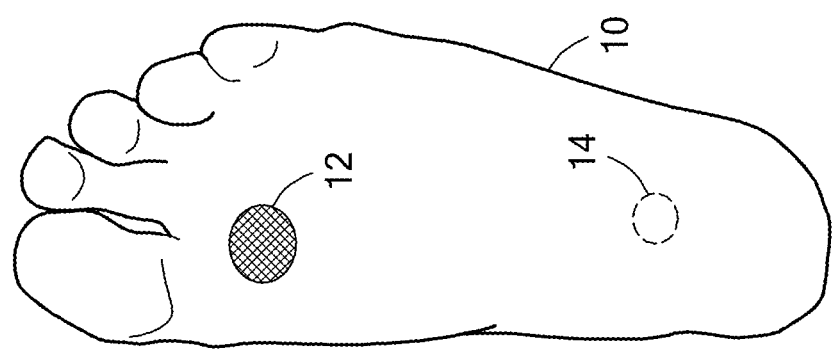
FIG. 1 schematically shows a foot having a prominent foot ulcer and a pre-ulcer.

FIG. 1 schematically shows a bottom view of the sole of a person's foot 10 (the person also is referred to as a "patient") that, undesirably, has an ulcer 12 and a pre-ulcer 14 (described below and shown in phantom since pre-ulcers 14 do not break through the skin). As one would expect, an ulcer 12 on this part of the foot 10 typically is referred to as a "foot ulcer 12." Generally speaking, an ulcer is an open sore on a surface of the body generally caused by a breakdown in the skin or mucous membrane. Diabetics often develop foot ulcers 12 on the soles of their feet 10 as part of their disease. In this setting, foot ulcers 12 often begin as a localized inflammation that may progress to skin breakdown and infection.

It should be noted that discussion of diabetes and diabetics is but one example and used here simply for illustrative purposes only. Accordingly, various embodiments apply to other types of diseases (e.g., stroke, deconditioning, sepsis, friction, coma, etc.) and other types of ulcers—such embodiments may apply generally where there is a compression or friction on a person's body over an extended period of time. Moreover, illustrative embodiments apply to footwear used by living beings other than people, such as other mammals (e.g., horses or dogs). Accordingly, discussion of diabetic human patients having foot ulcers 12 is for simplicity only and not intended to limit all embodiments of the invention.

Many prior art ulcer detection technologies known to the inventors suffered from one significant problem—patient compliance. If a diseased or susceptible patient does not regularly check his/her feet 10, then that person may not learn of an ulcer 12 or a pre-ulcer 14 until it has emerged through the skin and/or requires significant medical treatment. To solve that problem, illustrative embodiments implement an ulcer monitoring system as footwear that a person may use as part of their everyday routine, facilitating regular use.

Figure 2:
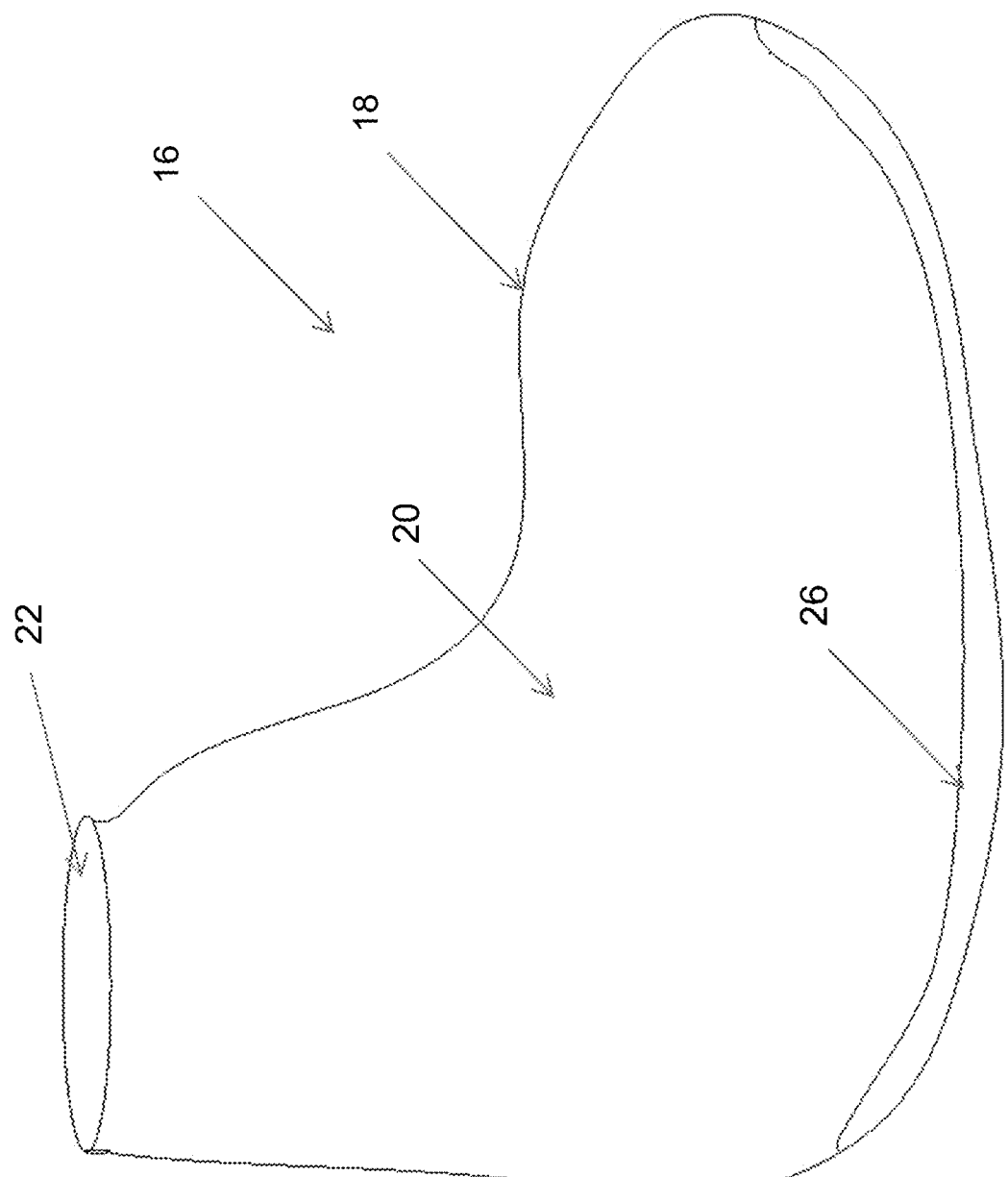
FIG. 2 schematically shows footwear that may implement illustrative embodiments of the invention.

To that end, FIG. 2 schematically shows a single piece of footwear 16 that may be configured in accordance with illustrative embodiments of the invention. This footwear may be used alone or in conjunction with another piece of identical or similarly functioning footwear. As known by those skilled in the art, footwear 16 is generally known as an item or garment that is worn on one's foot/feet. For example, the footwear 16 of FIG. 2 may be a shoe (e.g., a dress shoe, a sneaker or a boot), a slipper (e.g., worn primarily around one's home or indoors), an orthosis (e.g., a medical boot, insole, or cast), a sock, or a stocking. Accordingly, the footwear 16 has a body 18 that forms an interior 20 for receiving a person's foot 10. In addition or alternatively, an insole may be part of the body 18, or a separable part of the body 18 (e.g., a stand-alone apparatus that can be inserted into and removed from the body 18). An opening 22 near the top of the body 18 enables the person to put their foot 10 into the interior 20.

As known in the art, if formed as a shoe or a slipper, the body 18 may be formed to be relatively rigid (e.g., formed from a hard or soft plastic, fabric, resin, or leather), and yet have some flexibility at some or all of its portions to move as the foot 10 moves. In fact, even if formed as a sock, the body 18 may have some relatively rigid portion. However, illustrative embodiments formed as a sock generally have flexible bodies formed from a correspondingly flexible material, such as fabric, leather, or plastic.

Figure 3A:
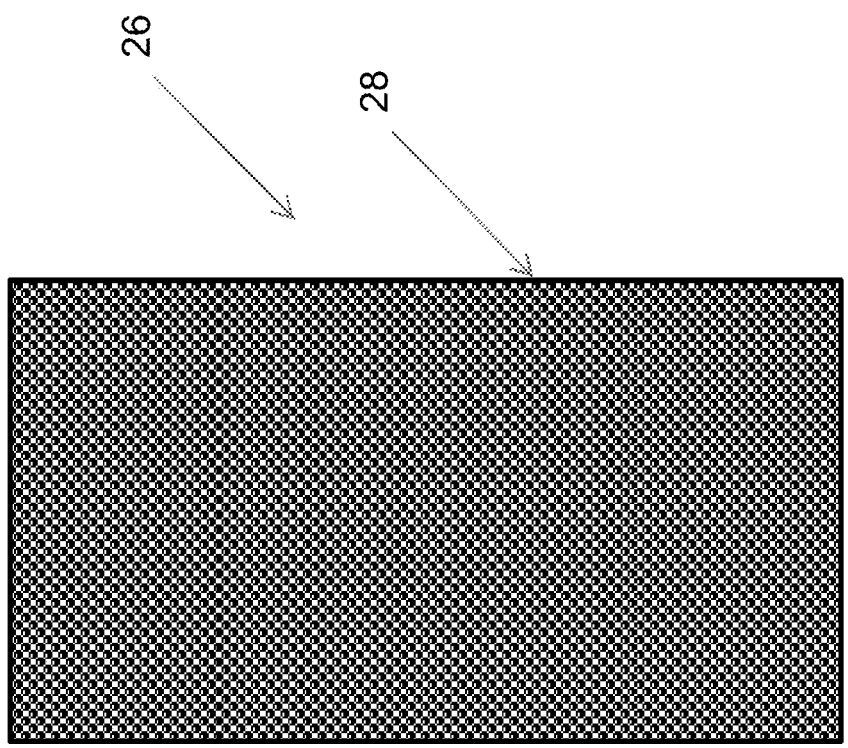
FIG. 3A schematically shows a matrix of temperature sensors within the footwear of FIG. 2A configured in accordance with illustrative embodiments of the invention.

In accordance with illustrative embodiments of the invention, the interior 20 of the footwear 16 has a plurality of temperature sensors 26 that measure the temperature across a wide surface area of the foot 10 (e.g., across part or all of the sole of the foot). Specifically, the plurality of temperature sensors 26 preferably are positioned in a two dimensional array (also identified by reference number "26") to form a sensor matrix (discussed below). FIG. 3A schematically shows a plan view of a sensor matrix that may be positioned within the interior 20 of the footwear body 18 of FIG. 2. It should be noted that although this plan view is generally rectangular, such a representation is merely schematic and thus, one of ordinary skill in the art can shape the array 26 to appropriately fit within the body interior 20 and/or conform to the shape of a human foot 10.

The temperature sensors 26 are positioned on a relatively large printed circuit board 28. More specifically, the temperature sensors 26 preferably are laid out in a two-dimensional array/matrix 26 on the printed circuit board 28. In various embodiments, the temperature sensors 26 are stationary relative to the printed circuit board 28. The pitch or distance between the various sensors 26 preferably is relatively small, thus permitting a high sensor density on the array 26. To more readily conform to the three-dimensional shape of a person's foot 10, the printed circuit board 28 preferably is formed largely from a flexible material that supports the array of temperature sensors 26. For example, the printed circuit board 28 may be formed primarily from a flex circuit. As another example, the printed circuit board 28 may be formed from strips of material that individually flex when receiving feet. See the incorporated patent applications for additional examples of such printed circuit boards 28.

Accordingly, when the body 18 receives a person's foot 10, a flexible surface within the interior 20 at least in part conforms to the shape of the person's foot 10. Specifically, when the body interior 20 receives the foot 10, the inner surface of the interior 20 having the temperature sensors 26 preferably at least in part conforms to the three-dimensional geometry of the sole of the person's foot 10. For example, this surface should conform to the arch of the foot 10.

Accordingly, to detect temperatures across the entire sole, the two-dimensional array should be larger than the length and the width of the foot 10. Such an embodiment therefore may monitor foot health for part or all of the sole. In alternative embodiments, however, the two dimensional array of temperature sensors 26 may be smaller than the length and/or the width of the foot 10 and thus, only monitor a portion of the foot 10. When used with a shoe or slipper, for example, the sensor array 26 and its printed circuit board 28 may be formed on a flexible insole (FIG. 2, also reference number 26) within the interior 20 of the body 18. Other embodiments may simply form the printed circuit board 28 and/or temperature sensors 26 directly into the structure of the body 18 itself (e.g., in a sock modality).

Among other things, the temperature sensors 26 may include stationary temperature sensitive resistors (e.g., printed or discrete components mounted onto the circuit board 28), thermocouples, fiberoptic temperature sensors, or a thermochromic film. Other embodiments may use non-contact temperature sensors 26, such as infrared detectors. Indeed, in that case, the temperature sensors 26 have a line of sight from the sensors 26 to the sole of the foot 10. Accordingly, discussion of contact sensors 26 is by example only and not intended to limit various embodiments.

Figure 3B:
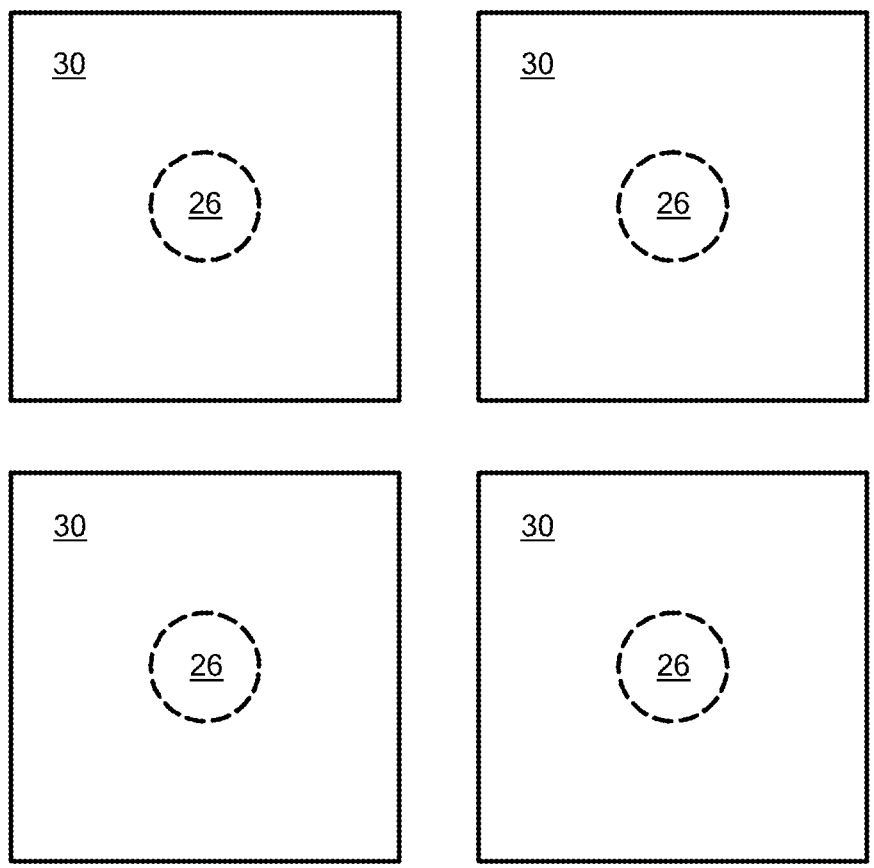
FIG. 3B schematically shows a close up view of the sensor array with details of the pads and temperature sensors.

To reduce the time required to sense the temperature at specific points, illustrative embodiments position an array of heat conducting pads 30 over the array of temperature sensors 26. To illustrate this, FIG. 3B schematically shows a small portion of the array of temperature sensors 26 showing four temperature sensors 26 and their pads 30. The temperature sensors 26 are drawn in phantom because they preferably are covered by the pads 30. Some embodiments do not cover the sensors 26, however, and simply thermally connect the sensors 26 with the pads 30.

Accordingly, each temperature sensor 26 has an associated heat conducting pad 30 that channels heat from one two dimensional portion of the foot 10 (considered a two dimensional area although the foot 10 may have some depth dimensionality) directly to its exposed surface. The array of conducting pads 30 preferably takes up the substantial majority of the total surface area of the printed circuit board 28. The distance between the pads 30 thermally isolates them from one another, thus eliminating thermal short-circuits.

For example, each pad 30 may have a square shape with each side having a length of between about 0.05 and 1.0 inch. The pitch between pads 30 thus is less than that amount. Accordingly, as a further detailed example, some embodiments may space the temperature sensors 26 about 0.4 inches apart with 0.25 inch (per side) square pads 30 oriented so that each sensor 26 is at the center of the square pads 30. This leaves an open region (i.e., a pitch) of about 0.15 inches between the square pads 30. Among other things, the pads 30 may be formed from a film of thermally conductive metal, such as a copper.

Some embodiments also may use pressure sensors for various functions, such as to determine the orientation of the feet 10, to measure the weight of the user, and/or to automatically begin the measurement process. Among other things, the pressure sensors may include piezoelectric, resistive, capacitive, or fiber-optic pressure sensors. The printed circuit board 28 also may have additional sensor modalities beyond temperature sensors 26 and pressure sensors, such as positioning sensors, GPS sensors, accelerometers, gyroscopes, communication interfaces for wireless and/or wired data transmission, and others known by those skilled in the art. A communication interface 44 (FIGS. 5 and 6) may connect wirelessly or through a wired connection with a larger network 32, implementing any of a variety of different data communication protocols, such as Ethernet. Alternatively, the communication interface 44 can communicate through an embedded Bluetooth or other short range wireless radio that communicates with a cellular telephone network (e.g., a 3G or 4G network).

The sensor array 26 is expected to receive significantly repeated forces, stresses, and pressures, which, if not properly manufactured, could damage the footwear 16. Accordingly, the temperature sensors 26 and associated components preferably are ruggedized to withstand the rigors of repeated shock caused by a person walking or running. Those skilled in the art can select the appropriate materials and configuration of the sensors to maximize their lifespans. In some embodiments, the intelligent functionality is replaceable and, in that case, preferably formed from relatively inexpensive components. For example, an old insole having the noted functionality may be removed from the inside of a shoe, and replaced with a new insole having the noted functionality. Various other embodiments also may encapsulate the electronics to be waterproof, such as by coating the printed circuit board 28 with a thermally transmissive, robust epoxy or polymer. Footwear 16 implemented as a sock can benefit from such a coating. Thermally conductive pads between the foot 10 and the array 26 also can prolong lifespan.

Figure 4:
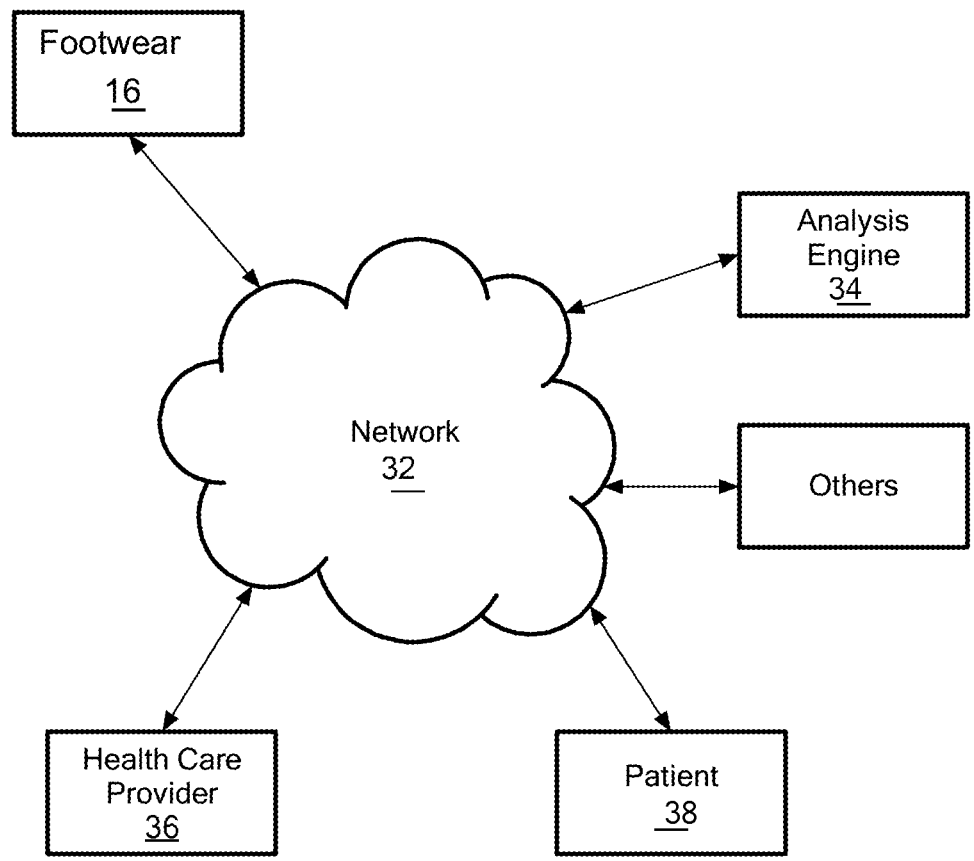
FIG. 4 schematically shows a network implementing of illustrative embodiments of the invention.

Although it gathers temperature and other data about the patient's foot 10, the footwear 16 may be part of a footwear system with additional logic located locally and/or remotely. For example, such additional logic may be on a remote computing device (e.g., a server 46, discussed below) across the Internet. To that and other ends, FIG. 4 schematically shows one way in which the footwear 16 can communicate with a larger data network 32 in accordance with various embodiments the invention. As shown, the footwear 16 may connect with the Internet through a local router, through its local area network, or directly without an intervening device. This larger data network 32 (e.g., the Internet) can include any of a number of different endpoints that also are interconnected. For example, the footwear 16 may communicate with a local or remote analysis engine 34 (discussed below) that analyzes the thermal data from the footwear 16 and determines the health of the patient's foot 10. The footwear 16 also may communicate directly with a healthcare provider 36, such as a doctor, nurse, relative, and/or organization charged with managing the patient's care. In fact, the footwear 16 also can communicate with the patient 38 (identified only in FIG. 4 as reference number 38), such as through text message, telephone call, e-mail communication, or other modalities as the system permits.

Figure 5:
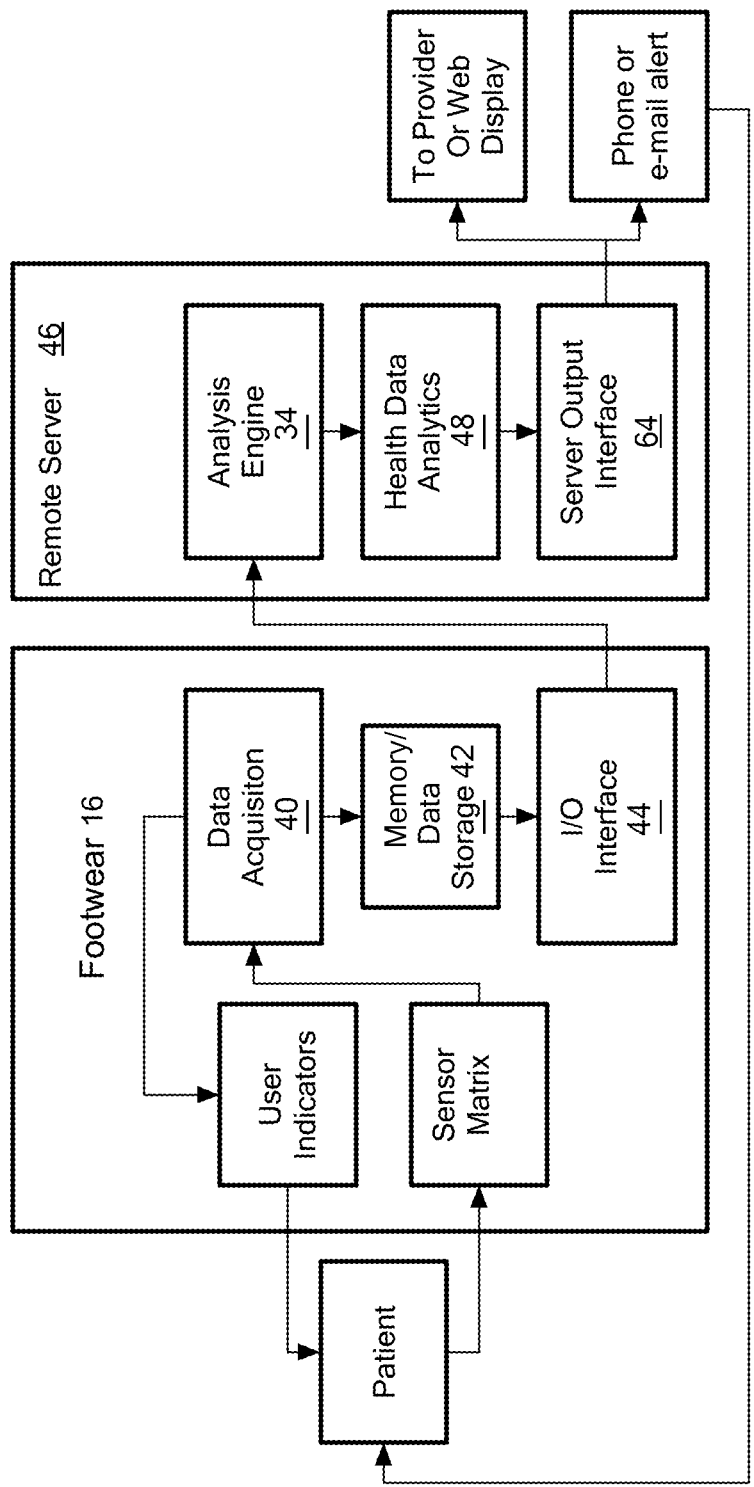
FIG. 5 schematically shows an overview of various components of illustrative embodiments of the invention.

FIG. 5 schematically shows a block diagram of one implementation of a foot monitoring system/footwear system, showing the footwear platform and the network 32 with its interconnected components in more detail. As shown, a data acquisition block 40 controls acquisition of the temperature and other data from the sensor array 26 for storage in a data storage device 42 (all memory and storage devices are identified by reference number "42" regardless of the location of the memory). Among other things, the data storage device 42 can be a volatile or nonvolatile storage medium, such as a hard drive, high-speed random-access-memory ("RAM"), or solid-state memory. The input/output interface port 44 selectively transmits or forwards the acquired data from the storage device 42 to the analysis engine 34, which may be local to the footwear 16/body 18, on a remote computing device, such as the prior mentioned remote server 46, or distributed locally and remotely as such. The data acquisition block 40 also may control optional user indicators/displays (not shown), which may provide feedback to the user, such as an audible, visual, or tactile medium.

As noted above and discussed in greater detail below with regard to FIGS. 7 and 8, the analysis engine 34, on the remote server 46 in this example, analyzes the data received from the footwear 16 in conjunction with a health data analytics module 48. A server output interface 64 forwards the processed output information/data from the analysis engine 34 and health data analytics module 48 as an output message toward others across the network 32, such as to a provider, a web display, or to the user via a phone, e-mail alert, text alert, or other similar way.

This output message may have the output information in its relatively raw form for further processing. Alternatively, this output message may have the output information formatted in a high-level manner for easy review by automated logic or a person viewing the data. Among other things, the output message may indicate the actual emergence of an ulcer 12 or a pre-ulcer 14, the risk of the emergence of an ulcer 12 or a pre-ulcer 14, the progression of a known ulcer 12 or pre-ulcer 14, or simply that the foot 10 is healthy and has no risks of ulcer 12 or pre-ulcer 14. In addition, this output message also may have information that helps an end-user or healthcare provider 36 monitor an ulcer 12 or pre-ulcer 14.

Using a distributed processing arrangement like that shown in FIG. 5 has a number of benefits. Among other things, it permits the footwear 16 to have relatively simple and inexpensive components that are unobtrusive to the patient 38. Moreover, this permits a "software-as-a-service" business model ("SAAS model"), which, among other things, permits more flexibility in the functionality, typically easier patient monitoring, and more rapid functional updates. In addition, the SAAS model facilitates accumulation of patient data to improve analytic capability.

As noted, some embodiments may distribute and physically position the functional components in a different manner. For example, the footwear 16 may have the analysis engine 34, or portions of the analysis engine 34, embedded within its body 18 and/or interior 20. In fact, some embodiments provide the functionality entirely in the footwear 16 and/or within other components in the local vicinity of the footwear 16. Accordingly, discussion of a distributed footwear system is but one of a number of embodiments that can be adapted for a specific application or use.

Figure 6:
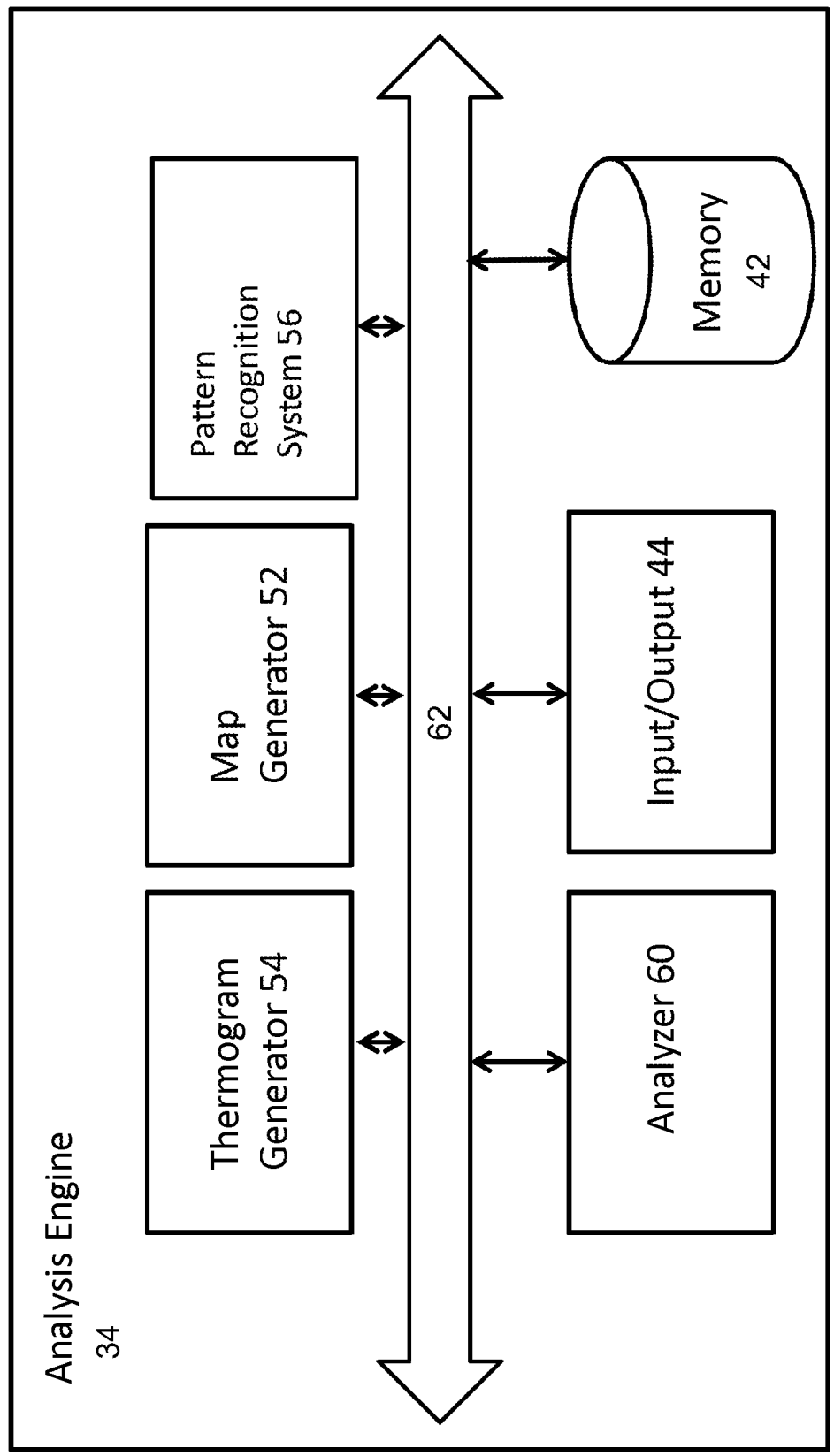
FIG. 6 schematically shows details of an analysis engine/analyzer configured in accordance with illustrative embodiments of the invention.

FIG. 6 shows several functional blocks that, with other functional blocks, may be configured to perform the functions of the analysis engine 34. This figure simply shows the blocks and is illustrative of one way of implementing various embodiments, while FIGS. 7 and 8 describe some of their functions in greater detail.

Each of these components is operatively connected by any conventional interconnect mechanism. FIG. 6 simply shows a bus 62 communicating each the components. Those skilled in the art should understand that this generalized representation can be modified to include other conventional direct or indirect connections. Accordingly, discussion of the bus 62 is not intended to limit various embodiments.

Indeed, it should be noted that FIG. 6 only schematically shows each of these components. Those skilled in the art should understand that each of these components can be implemented in a variety of conventional manners, such as by using hardware, software, firmware, or a combination of hardware and software, across one or more other functional components. For example, the analysis engine 34 has a map generator 52, which may be implemented using a plurality of microprocessors executing firmware in a local memory 42. As another example, the map generator 52 may be implemented using one or more application specific integrated circuits (i.e., "ASICs") and related software, or a combination of ASICs, discrete electronic components (e.g., transistors), and microprocessors. Accordingly, the representation of the map generator 52 and other components in a single box of FIG. 6 is for simplicity purposes only. In fact, in some embodiments, the map generator 52 of FIG. 6 is distributed across a plurality of different machines—not necessarily within the same device.

It should be reiterated that the representation of FIG. 6 is a significantly simplified representation of an actual analysis engine 34. Those skilled in the art should understand that such a device may have many other physical and functional components, such as central processing units, other processing modules, and short-term memory 42. Accordingly, this discussion is not intended to suggest that FIG. 6 represents all of the elements of the analysis engine 34.

In summary, the analysis engine 34 of FIG. 6 has the prior mentioned map generator 52 configured to form a temperature map from the plurality of discrete temperature data values. As discussed in greater detail below, a temperature map is a collection of geometric, spatial and temperature data. Specifically, a temperature map includes data representing 1) substantially the actual geometric shape and dimensions of at least a portion of the foot 10, and 2) the distribution of temperatures of at least a portion of the foot 10 across that actual geometric shape. Of course, the geometric shape and size has minor limitations relating to the granularity of the temperature readings—i.e., the total number of temperature readings/temperature sensors 26 in the sensor matrix. More low pitch temperature sensors 26 (i.e., temperature sensors 26 more closely positioned together) in a given area should provide a more accurate actual geometric shape of the sole of the foot 10. Thus, while ideally the actual shape is shown, in practice, illustrative embodiments only are able to reconstruct "substantially" the actual geometric shape with substantially actual measurements.

As discussed below, some embodiments form the temperature map as a pixelated data structure—it does not necessarily have a continuous temperature distribution across its geography. This data structure may be processed as data without being rasterized, or processed and rasterized.

Other embodiments, however, may form the temperature map in the form of a thermogram. Specifically, unlike the pixelated version, a thermogram provides a continuous temperature distribution, and also potentially to provides a more accurate geometric shape and size of the sole of the foot 10. Thus, the analysis engine 34 also may have an optional thermogram generator 54 configured to form a thermogram of the patient's foot 10 or feet 10 based on a plurality of temperature readings from the bottom of the foot 10.

In simple terms, as known by those in the art, a thermogram is a data record made by a thermograph, or a visual display of that data record. A thermograph simply is an instrument that records temperatures (i.e., the footwear 16). As applied to illustrative embodiments, a thermograph measures temperatures and generates a thermogram, which is data, or a visual representation of that data, of the continuous two-dimensional temperature data across some physical region, such as a foot 10. Accordingly, unlike an isothermal representation of temperature data, a thermogram provides a complete, continuous data set/map of the temperatures across an entire two-dimensional region/geography. More specifically, in various embodiments, a thermogram shows (within accepted tolerances) substantially complete and continuous two-dimensional spatial temperature variations and gradients across portions of the sole of (at least) a single foot 10, or across the entire sole of the single foot 10.

The analysis engine 34 also has a pattern recognition system 56 configured to determine whether the temperature map, in whichever form, presents any of a number of different prescribed patterns. Pattern data and other information may be stored in a local memory 42. As discussed below, if the temperature map presents any of these prescribed patterns, then the foot 10 may be unhealthy in some manner (e.g., having a pre-ulcer 14 or an ulcer 12).

The analysis engine 34 also has an analyzer 60 configured to produce the above noted output information, which indicates any of a number of different conditions of the foot 10. For example, the output information may indicate the risk that an ulcer 12 will emerge, the emergence of an ulcer 12 and/or pre-ulcer 14 (i.e., the first indication of an ulcer 12 and/or pre-ulcer 14), and/or the progression of a known ulcer 12/pre-ulcer 14. Communicating through some interconnect mechanism, such as the noted bus 62 or network connection, these modules cooperate to determine the status of the foot 10, which may be transmitted or forwarded through a local input/output port 44 that communicates with the prior noted parties across the larger data network 32.

As shown in FIG. 5, the analysis engine 34 of FIG. 6 may be physically positioned at a remote location from the footwear 16—in this example, on the server 46. In that case, the matrix of temperature sensors 26 in the footwear interior 20 communicates with the analysis engine 34 using its local input/output interface 44. Other embodiments, however, may distribute the components of the analysis engine 34 between the server 46 and the footwear 16. For example, the footwear 16 may include the map generator 52 (e.g., integrated into the footwear 16), while the server 46 may include the remaining components. Other embodiments, however, include the entire analysis engine 34 within the body 18 of the footwear 16—they are integrated as part of the footwear 16. Those skilled in the art can select the appropriate arrangement for a given application.

Figure 7:
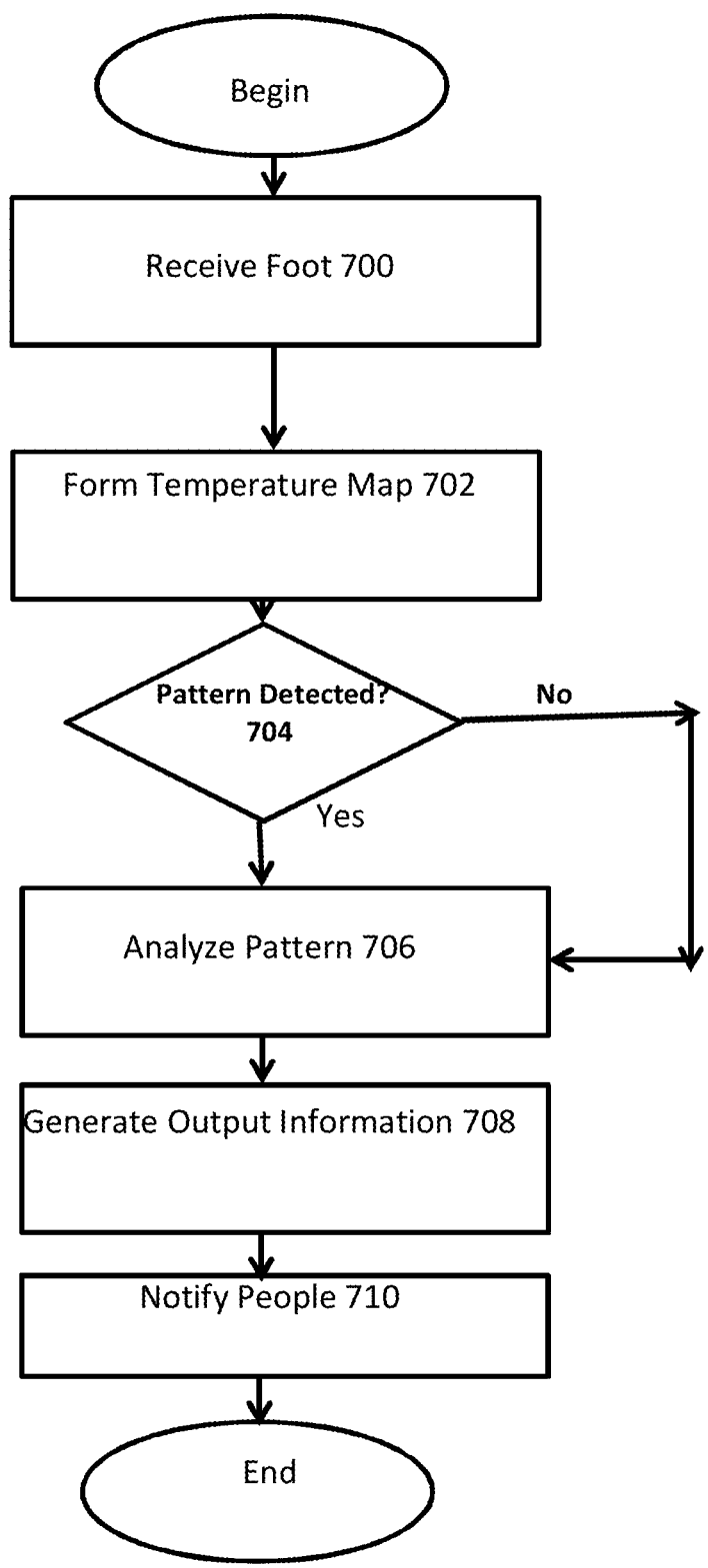
FIG. 7 shows a process of monitoring the health of the person's foot or feet in accordance with illustrative embodiments the invention.
Figure 8:
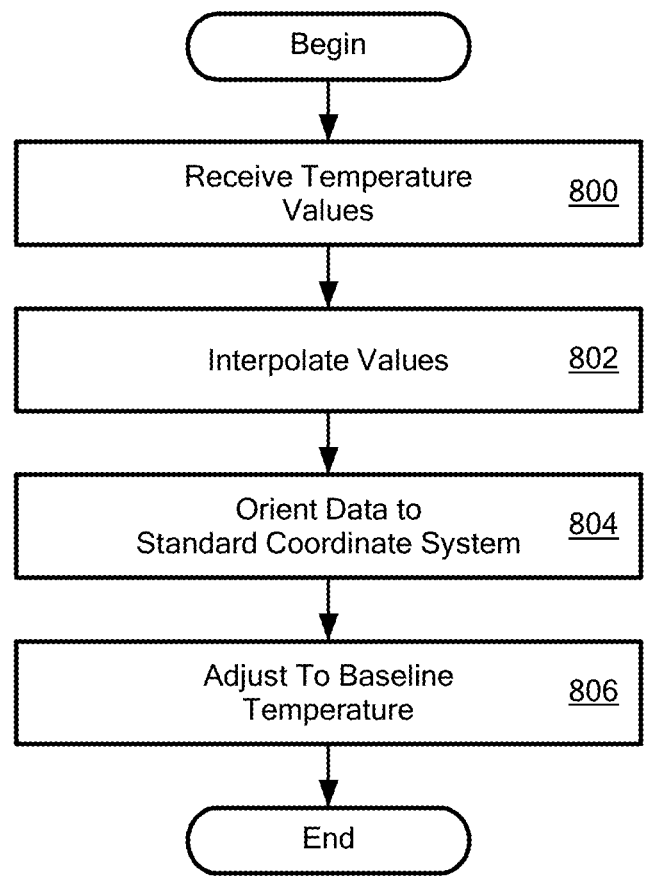
FIG. 8 shows a process of forming a thermogram in accordance with alternative embodiments of the invention.

FIG. 7 shows a process that uses the various components described above in FIGS. 1 through 6 to determine the health of the patient's foot 10. It should be noted that this process is a simplified, high level summary of a much larger process and thus, should not be construed to suggest that only these steps are required. In addition, some of the steps may be performed in a different order than those described below. Although functions and processes of this process are described as being executed by the functional blocks in FIGS. 5 and 6, some embodiments can be executed by other functional components.

The process begins at step 700, in which the footwear 16 receives a person's foot 10. Specifically, a person simply inserts their foot 10 through the opening 22 in the footwear 16 and into the interior 20 of the footwear body 18. At this point, the foot preferably is snugly positioned within the interior 20 of the body 18 (e.g., via shoelace tightening or the flexibility of the body 18). Presumably, the sensors and other logic are energized before the footwear 16 receives the person's foot 10. Some embodiments, however, may require that the footwear 16 be affirmatively energized by the person turning on power in some manner (e.g., actuating a power switch to use local battery power). Other embodiments, however, normally may operate in a low power, conservation mode (a "sleep mode") that rapidly turns on in response to a stimulus, such as receipt of the person's foot 10. When using local battery power, some embodiments may implement rechargeable batteries and/or energy scavenging devices that generate energy from the motion of the foot (e.g., using microelectromechanical systems devices, such as accelerometers).

Next, the process continues to step 702, in which the map generator 52 forms a temperature map of the sole of the person's foot 10. Specifically, as noted above, a temperature map includes data representing 1) substantially the actual geometric shape and size of at least a portion of the foot 10, and 2) the distribution of temperatures of the at least a portion of the foot 10 across that actual geometric shape.

To that end, the map generator 52 or other logic controls the sensor array 26 to begin measuring the temperature across the person's foot/sole. The map generator 52 and other logic does not necessarily have preconceived or prescribed information associating any one or more temperature sensors 26 to any specific anatomy of the foot 10. Instead, the map generator 52 simply receives the plurality of discrete temperature data values from the two dimensional array of temperature sensors 26. Using this data, the map generator 52 produces a geometric shape that represents substantially the actual geometric shape and dimensions of at least a portion of the foot 10 (aka "foot geometry"). For example, the map generator 52 may produce a geometric shape of the entire foot 10, or just one or more selected portions of the foot 10 (e.g., the heel, big toe, ball of the foot 10, etc.).

The map generator 52 may use any of a wide variety of techniques to form the geometric shape. For example, the map generator 52 may simply locate the boundary of the foot 10 by detecting significant temperature differences between adjacent or nearly adjacent temperature sensors 26. Alternatively, temperature sensors 26 that are close in temperature to the ambient or environmental temperature, as measured (for example) by an external sensor, may be considered to be outside the foot boundary, while and those temperature sensors 26 significantly above the ambient temperature may be considered to be inside the foot boundary. In another embodiment, certain temperature sensors 26 may be cut off of the array 26 to enable a better fit onto the foot 10 (e.g., an insole cut to the same shape as the foot before inserting into the shoe), and the map generator 52 may detect which sensors remain attached and are therefore considered inside the foot boundary.

To avoid potential false boundaries, some embodiments may identify a certain generalized area of the array 26, such as some radial distance away from the center of the array 26, as not a boundary of the foot 10. The determined boundary may be stored in memory 42 or otherwise used to receive the temperature distribution. Alternative embodiments may form a thermogram from the discrete temperature values to determine the boundary and temperature distribution. The thermogram implementation is discussed below with regard to FIG. 8.

Before, during, or after forming the geometric shape, the map generator 52 may generate the above noted temperature distribution across the specific geometry of the foot 10. Next, the map generator 52 populates the geometric shape with the temperature distribution to complete the temperature map.

In some embodiments, the foot geometry is not a separate step from populating the temperature distribution. In that case, the map generator 52 simply displays all of the temperatures across the region it measured. If the granularity of the temperature readings/array is fine enough, it should form the boundary representing the substantially the actual shape of at least a portion of the foot 10, thus producing the temperature map.

Figure 9A:
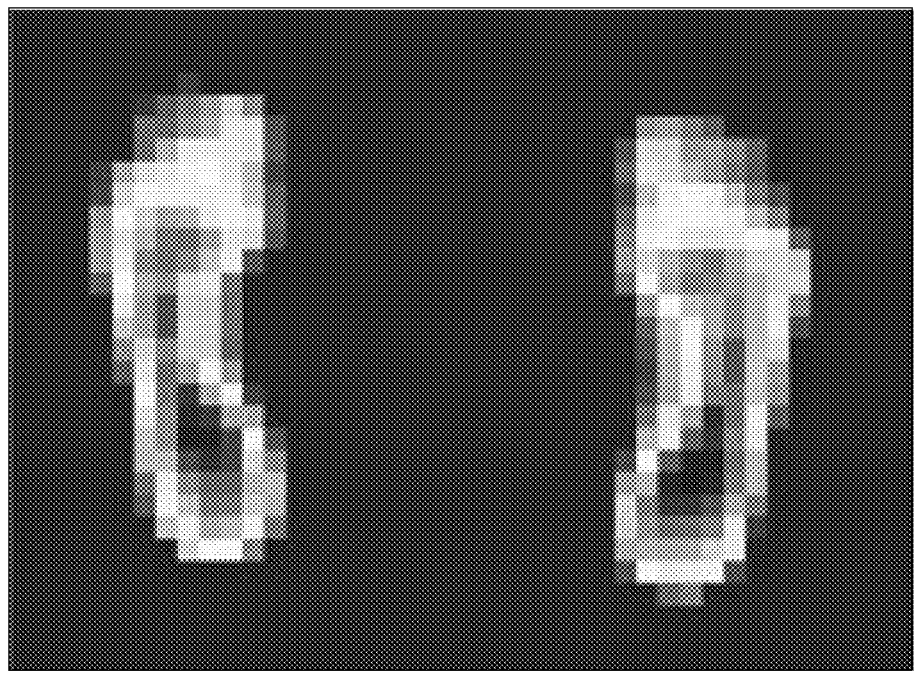
FIGS. 9A-9D schematically show the progression of a thermogram and how it is processed in accordance with one embodiment of the invention.
Figure 9B:

FIG. 9A schematically shows an example of a temperature map (of two feet using a pair of footwear 16 configured as noted) formed using this technique. As discrete temperature values, this representation does not have temperature information for the regions of the foot 10 between the temperature sensors 26. In addition, the boundary may be somewhat aliased due to the digital nature of the temperature sensors 26. FIG. 9B schematically shows a temperature map of the same two feet using the thermogram technique, discussed below with regard to FIG. 8.

The temperature sensors 26 may take a relatively long time to ultimately make their readings. For example, this process can take between 30 to 60 seconds. If the footwear 16 is used for normal, routine daily use, then such a time should not pose such a problem. However, for footwear 16 used primarily to detect ulcers 12 or pre-ulcers 14, such as a period may present an obstacle to compliance. Accordingly, illustrative embodiments of the invention do not require such long data acquisition periods. Instead, the footwear system can use conventional techniques to extrapolate a smaller amount of real temperature data (e.g., a sparser set of the temperature data) to arrive at an approximation of the final temperature at each point of the foot 10. For example, this embodiment may use techniques similar to those used in high speed thermometers to extrapolate the final temperature data using only one to three seconds of actual temperature data. Of course, various embodiments may not use this expedited technique and simply wait the noted amount of time to obtain the temperature readings.

Figure 9C:
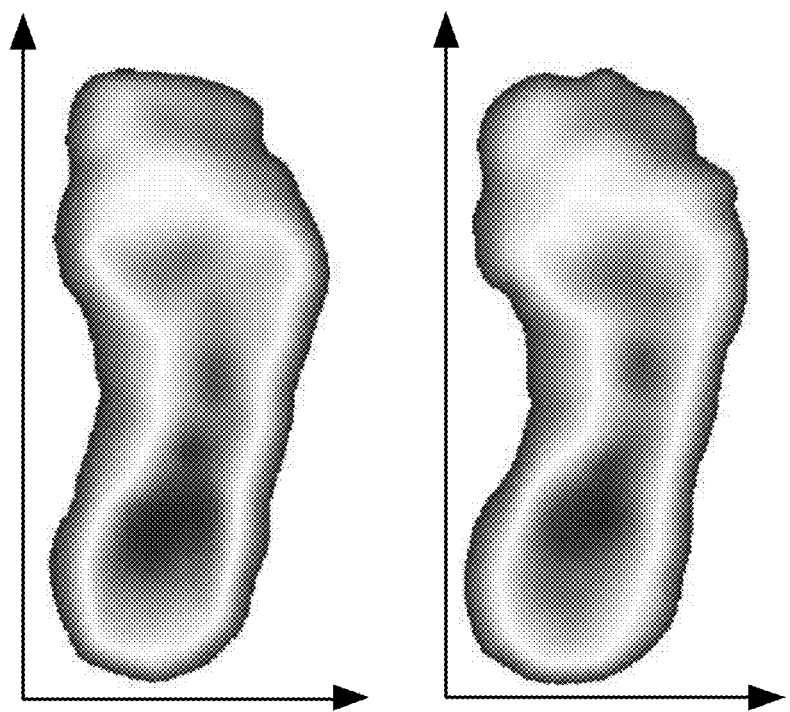

The map generator 52 or other part of the analysis engine 34 next preferably orients the temperature map to a standard coordinate system. Specifically, the process transforms the temperature map into a standard coordinate system for comparison against other temperature measurements on the same foot 10, and on the other foot 10. This ensures that the analyzer 60 can compare prescribed whichever portions of the foot/feet 10 necessary. For example, when properly oriented, each portion of one foot 10 may be compared to itself from an earlier temperature map, and/or a corresponding portion on the other foot 10. FIG. 9C schematically shows one example of how this step may reorient the temperature map of FIG. 9B. Note that although FIG. 9C shows a thermogram implementation, those skilled in the art may apply its teachings to the discrete implementation shown in FIG. 9A.

The position and orientation of the foot 10 within the logic of the system therefore may be important when performing this step. For example, to determine the position and orientation of the foot 10, the analysis engine 34 and its map generator 52 simply may contrast the regions of elevated temperature on the array 26 (i.e., due to foot contact) with those at ambient temperature. Finally, the map generator 52 may orient the foot 10 to align with another foot 10 (e.g., if comparing two feet) or to align it with the same foot 10 from another reading. If there is no other foot 10 to compare against, however, the analysis engine 34 may orient the temperature map to a prescribed orientation, or not change its orientation.

Now that the map generator 52 has produced the properly oriented temperature map, the pattern recognition system 56 determines if the temperature map presents or shows any of a number of prescribed patterns (step 704). The analyzer 60 next analyzes any detected pattern (step 706) to determine if there are hotspots. In particular, as noted, an elevated temperature at a particular portion of the foot 10 may be indicative or predictive of the emergence and risk of a pre-ulcer 14 or ulcer 12 in the foot 10. For example, temperature deviations of about 2 degrees C. or about 4 degrees F. in certain contexts can suggest emergence of an ulcer 12 or pre-ulcer 14. Temperature deviations other than about two degrees C. also may be indicative of a pre-ulcer 14 or ulcer 12 and thus, 2 degrees C. and 4 degrees F. are discussed by example only. Accordingly, various embodiments analyze the temperature map to determine if the geography of the foot 10 presents or contains one or more of a set of prescribed patterns indicative of a pre-ulcer 14 or ulcer 12. Such embodiments may analyze the visual representation of the temperature map, or just the data otherwise used to generate and display a temperature map image—without displaying the temperature map.

A prescribed pattern may include a temperature differential over some geography or portion of the foot 10 or feet 10. To that end, various embodiments contemplate different patterns that compare at least a portion of the foot 10 against other foot data. Among other things, those comparisons may include the following:

1. A comparison of the temperature of the same portion/spot of the same foot 10 at different times (i.e., a temporal comparison of the same spot),
2. A comparison of the temperatures of corresponding portions/spots of the patient's two feet 10 at the same time or at different times, and/or
3. A comparison of the temperature of different portions/spots of the same foot 10 at the same time or at different times.

Figure 10A:
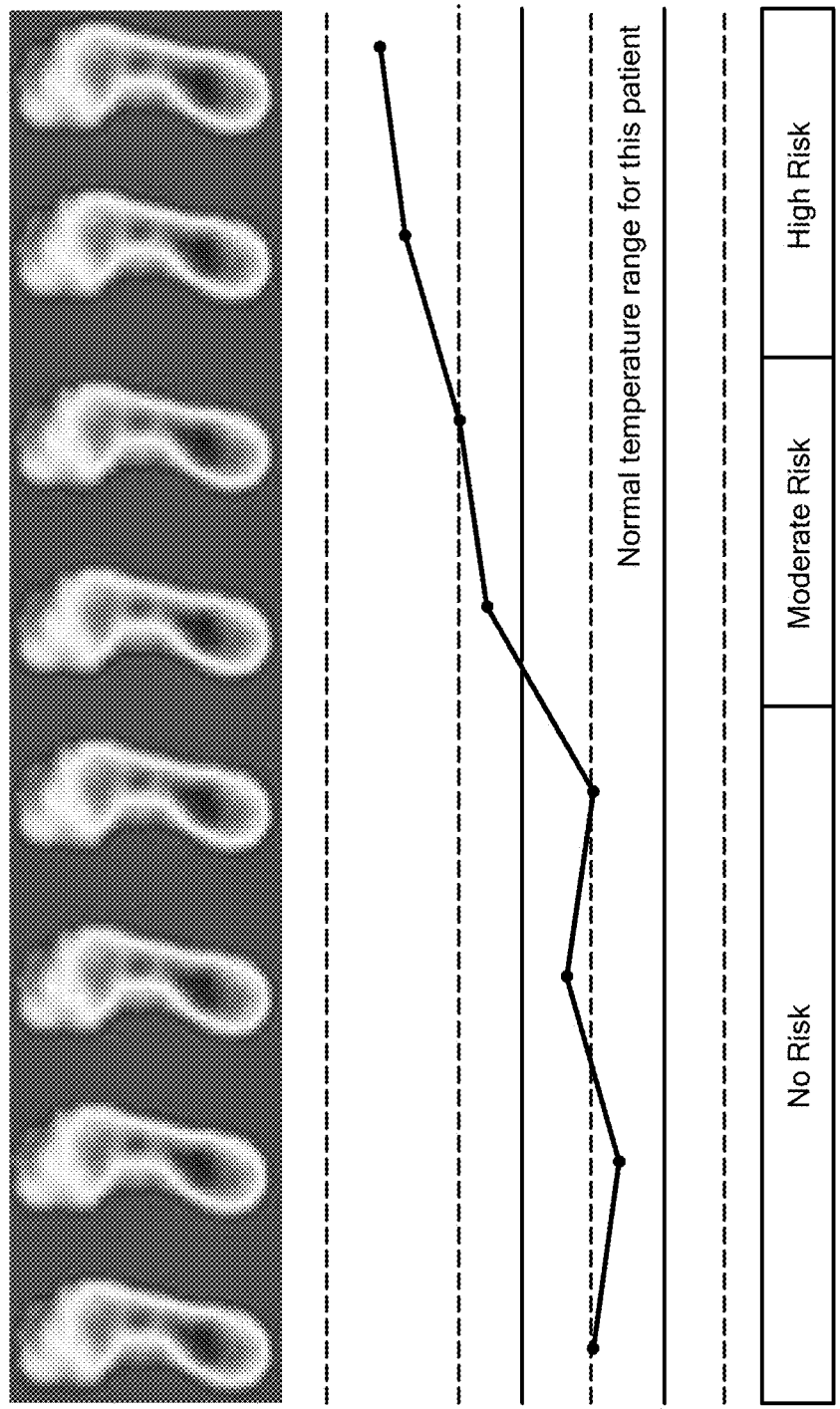
FIGS. 10A and 10B schematically show two different types of patterns that may be on the soles of a person's foot indicating an ulcer or pre-ulcer.

As an example of the first comparison, the pattern may show a certain region of a foot 10 has a temperature that is 4 F higher than the temperature at that same region several days earlier. FIG. 10A schematically shows one example of this using a thermogram implementation, in which a portion of the same foot 10—the patient's left foot 10, has a spot with an increased risk of ulceration.

Figure 10B:
Figure 10B:

As an example of the second comparison, the pattern may show that the corresponding portions of the patient's feet 10 have a temperature differential that is 4 degrees F. FIG. 10B schematically shows an example of this, where the region of the foot 10 on the left (the right foot 10) having a black border is hotter than the corresponding region on the foot 10 on the right (the left foot 10).

As an example of the third comparison, the pattern may show localized hotspots and peaks within an otherwise normal foot 10. These peaks may be an indication of pre-ulcer 14 or ulcer 12 emergence, or increased risk of the same, which, like the other examples, alerts caregiver and patient to the need for more vigilance.

Of course, various embodiments may make similar comparisons while analyzing the temperature map for additional patterns. For example, similar to the third comparison, the pattern recognition system 56 may have a running average of the temperature of the geography of the entire foot 10 over time. For any particular spot on the foot 10, this running average may have a range between a high temperature and a low temperature. Accordingly, data indicating that the temperature at that given spot is outside of the normal range may be predictive of a pre-ulcer 14 or an ulcer 12 at that location.

Some embodiments may use machine learning and advanced filtering techniques to ascertain risks and predictions, and to make the comparisons. More specifically, advanced statistical models may be applied to estimate the current status and health of the patient's feet 10, and to make predictions about future changes in foot health. State estimation models, such as a switching Kalman filters, can process data as they become available and update their estimate of the current status of the user's feet 10 in real-time. The statistical models can combine both expert knowledge based on clinical experience, and published research (e.g., specifying which variables and factors should be included in the models) with real data gathered and analyzed from users. This permits models to be trained and optimized based on a variety of performance measures.

Models can be continually improved as additional data is gathered, and updated to reflect state-of-the-art clinical research. The models also can be designed to take into account a variety of potentially confounding factors, such as physical activity (e.g., running), environmental conditions (e.g., a cold surrounding temperature, such as the outdoors during a cold day), personal baselines, past injuries, predisposition to developing problems, and problems developing in other regions (e.g., a rise in temperature recorded by a sensor 26 may be due to an ulcer 12 developing in a neighboring region measured by a different sensor). In addition to using these models for delivering real-time analysis of users, they also may be used off-line to detect significant patterns in large archives of historical data. For example, a large rise above baseline temperature during a period of inactivity may precede the development of an ulcer 12.

Alternative embodiments may configure the pattern recognition system 56 and analyzer 60 to perform other processes that identify risk and emergence, as well as assist in tracking the progressions ulcers 12 and pre-ulcers 14. For example, if there is no ambient temperature data from a temperature map prior to the patient's use of the footwear 16, then some embodiments may apply an Otsu filter (or other filter) first to the high resolution temperature map to identify regions with large temperature deviations from ambient. The characteristics of these regions (length, width, mean temperature, etc.) then may be statistically compared to known distributions of foot characteristics to identify and isolate feet 10. The right foot temperature map may be mirrored and an edge-alignment algorithm can be employed to standardize the data for hotspot identification.

Two conditions can be evaluated independently for hotspot identification. The first condition evaluates to true when a spatially-localized contralateral thermal asymmetry exceeds a pre-determined temperature threshold for a given duration. The second condition evaluates to true when a spatially-localized ipsilateral thermal deviation between temporally successive scans exceeds a pre-determined temperature threshold for a given duration. The appropriate durations and thermal thresholds can be determined from literature review or through application of machine learning techniques to data from observational studies. In the latter case, a support vector machine or another robust classifier can be applied to outcome data from the observational study to determine appropriate temperature thresholds and durations to achieve a desired balance between sensitivity and specificity.

Illustrative embodiments have a set of prescribed patterns against which the pattern recognition system 56 and analyzer 60 compare to determine foot health. Accordingly, discussion of specific techniques above are illustrative of any of a number of different techniques that may be used and thus, are not intended to limit all embodiments of the invention.

Some embodiments discussed above generally check for similar patterns across the entire foot 10. Alternative embodiments, however, check for different patterns at different points of the foot/feet. Specifically, such embodiments may use non-uniform temperature thresholds to evaluate risk and for determining what these thresholds ought to be to support monitoring with a target sensitivity and specificity. The temperature thresholds may depend on the anatomical location of the temperature difference in question, as well as the temperature differences preceding the most recent measurement chronologically. This permits more granular interpretation of risk into the monitoring.

For example, the contralateral asymmetry threshold for determining if the foot 10 presents a pattern indicative of inflammation may be at least 2.2 degrees C. at the midfoot, but at least 3.0 degrees at the hallux. In other words, this step may determine if the difference in temperature between two contralateral points/locations at the mid-foot is more than 2.2 degrees. At the same time, this step may determine if the difference in temperature difference between two contralateral points/locations at the hallux is more than 3.0 degrees.

Indeed, the dense array of temperature sensors 26 and corresponding temperature map enables many such pattern analysis techniques.

The process continues to step 708, which generates output information relating to the health of the foot 10. Specifically, at this stage in the process, the analysis engine 34 has generated the relevant data to make a number of conclusions and assessments, in the form of output information, relating to the health of the foot/feet 10. Among other things, those assessments may include the risk of an ulcer 12 or pre-ulcer 14 emerging anywhere on the foot 10, or at a particular location on the foot 10.

Figure 11A:
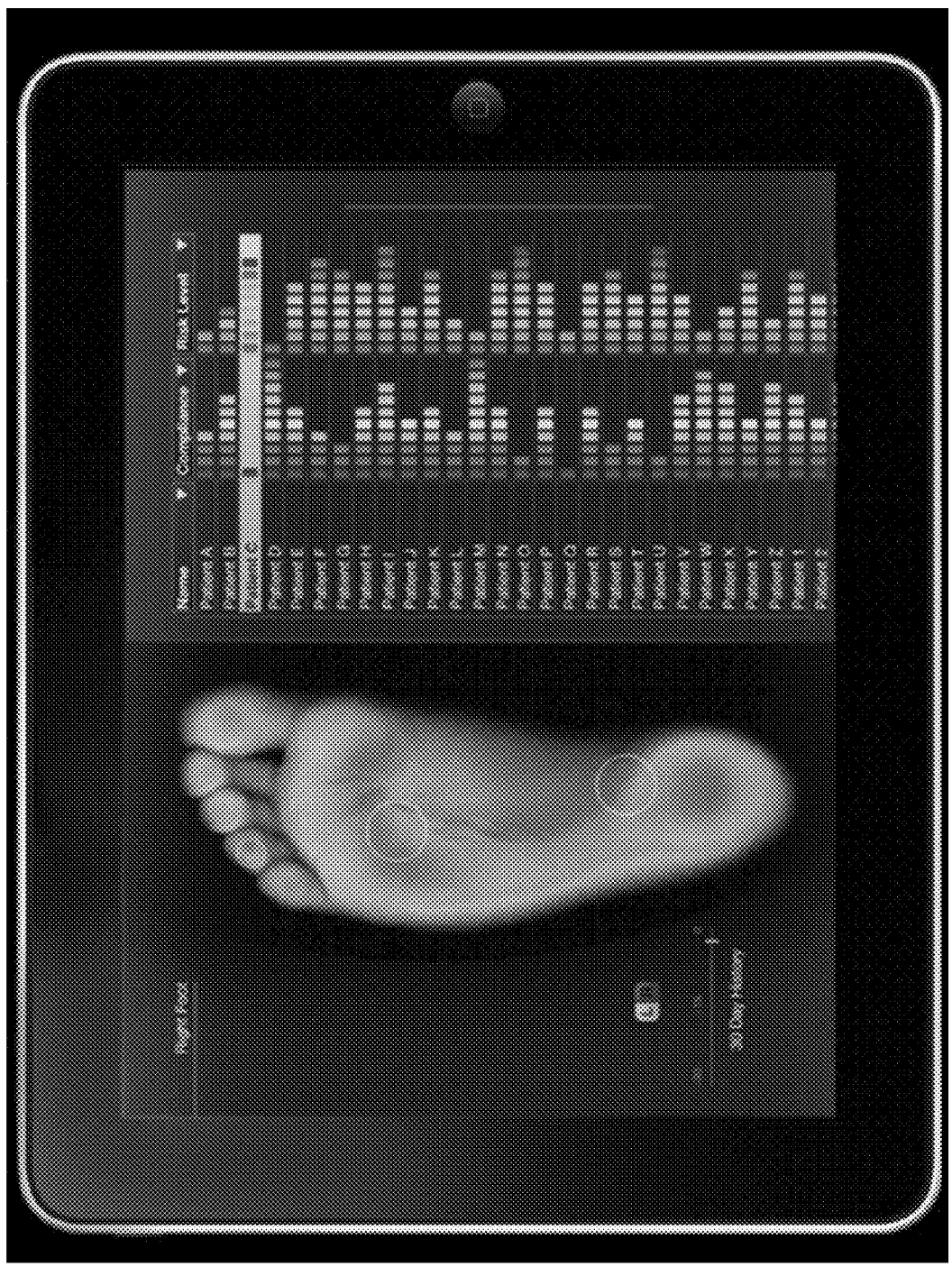
FIGS. 11A and 11B schematically show two different user interfaces that may be displayed in accordance with illustrative embodiments of the invention.
Figure 11B:
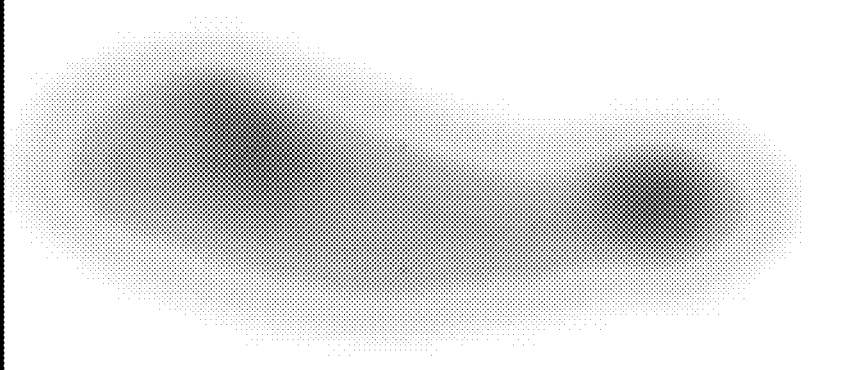

This risk may be identified on a scale from no risk to maximum risk. FIG. 11A shows one example of the output information in a visual format with a scale ranking the risk of ulcer emergence. The scale in this example visually displays de-identified patients (i.e., Patient A to Patient 2) as having a certain risk level of developing the foot ulcer 12. The "Risk Level" column shows one way of graphically displaying the output information, in which more rectangles indicate a higher risk of ulcer 12. Specifically, in this example, a single rectangle may indicate minimal or no risk, while rectangles filling the entire length of that table entry may indicate a maximum risk or fully emerged ulcer 12. Selection of a certain patient may produce an image of the foot 10 with a sliding bar showing the history of that patient's foot 10. FIG. 11B schematically shows a similar output table in which the risk level is characterized by a percentage from zero to hundred percent within some time frame (e.g., days). Patient C is bolded in this example due to their 80 percent risk of the emergence of an ulcer 12.

The output table thus may provide the caregiver or healthcare provider with information, such as the fact that Patient B has a 90 percent probability that he/she will develop a foot ulcer 12 in the next 4-5 days. To assist in making clinical treatment decisions, the clinician also may access the patient's history file to view the raw data.

As noted, some embodiments produce output information indicating the emergence of a pre-ulcer 14 at some spot on the foot 10. As known by those skilled in the art, a pre-ulcer 14 may be considered to be formed when tissue in the foot 10 is no longer normal, but it has not ruptured the top layer of skin. Accordingly, a pre-ulcer 14 is internal to the foot 10. More specifically, tissue in a specific region of the foot 10 may not be receiving adequate blood supply and thus, may need more blood. When it does not receive an adequate supply of blood, it may become inflamed and subsequently, become necrotic (i.e., death of the tissue). This creates a weakness or tenderness in that region of the foot 10. Accordingly, a callous or some event may accelerate a breakdown of the tissue, which ultimately may rupture the pre-ulcer 14 to form an ulcer 12.

Illustrative embodiments may detect the emergence of a pre-ulcer 14 in any of a number of manners described above. For example, the system may compare temperature readings to those of prior temperature maps, such as the running average of the temperature at a given location, the running average (or weighted average) of foot temperature, and/or the current average temperature of the foot 10 (e.g., an average of the discrete temperature data values of the most recent reading). This comparison may show an elevated temperature at that spot, thus signaling the emergence of a new pre-ulcer 14. In more extreme cases, this may indicate the actual emergence of a new ulcer 12.

The emergence or detection of a pre-ulcer 14 can trigger a number of other preventative treatments that may eliminate or significantly reduce the likelihood of the ultimate emergence of an ulcer 12. To that end, after learning about a pre-ulcer 14, some embodiments monitor the progression of the pre-ulcer 14. Preferably, the pre-ulcer 14 is monitored during treatment in an effort to heal the area, thus avoiding the emergence of an ulcer 12. For example, the caregiver may compare each day's temperature map to prior temperature maps, thus analyzing the most up to date state of the pre-ulcer 14. In favorable circumstances, during a treatment regimen, this comparison/monitoring shows a continuous improvement of the pre-ulcer 14, indicating that the pre-ulcer 14 is healing. The output information therefore can have current and/or past data relating to the pre-ulcer 14, and the risk that it poses for the emergence of an ulcer 12.

Sometimes, patients may not even realize that they have an ulcer 12 until it has become seriously infected. For example, if the patient undesirably does not use the footwear system for a long time, he/she may already have developed an ulcer 12. The footwear 16 then may produce output information indicating the emergence of an ulcer 12. To that end, the analyzer 60 may have prior baseline temperature information (i.e., data) relating to this patient's foot 10 (showing no ulcer 12), and make a comparison against that baseline data to determine the emergence of an actual ulcer 12. In cases where the data is questionable about whether it is an ulcer 12 or a pre-ulcer 14, the caregiver and/or patient nevertheless may be notified of the higher risk region of the foot 10 which, upon even a cursory visual inspection, should immediately reveal the emergence of an ulcer 12.

The process concludes at step 710, in which the process (optionally) manually or automatically notifies the relevant people about the health of the foot 10. These notifications or messages (a type of "risk message") may be in any of a number of forms, such as a telephone call, a text message, e-mail, and data transmission, or other similar mechanism.

For example, the system may forward an e-mail to a healthcare provider indicating that the right foot 10 of the patient is generally healthy, while the left foot 10 has a 20 percent risk of developing an ulcer 12, and a pre-ulcer 14 also has emerged on a specified region. Armed with this information, the healthcare provider may take appropriate action, such as by directing the patient to stay off their feet 10, use specialized footwear, soak their feet 10, or immediately check into a hospital.

As noted, some embodiments implement the temperature map as a thermogram. To that end, FIG. 8 shows a process of forming a thermogram in accordance with illustrative embodiments. Specifically, FIG. 8 shows a process that step 702 uses to form the temperature map as a thermogram for the embodiments that form a thermogram. It should be noted that, in a manner similar to FIG. 7, the process of FIG. 8 is a simplified, high level summary of a larger process and thus, should not be construed to suggest that only these steps are required. In addition, some of the steps may be performed in a different order than those described below. In a manner similar to the functions and processes of FIG. 7, the functions and processes described with regard to this process also can be executed by the functional blocks in FIGS. 5 and 6, or by other functional components.

The process of forming a thermogram begins at step 800, in which the thermogram generator 54 of the analysis engine 34 receives the plurality of temperature values, which, as noted above, are graphically shown by FIG. 9A. The thermogram generator 54 typically receives those temperature values as raw data. The depiction in FIG. 9A therefore is simply for illustration purposes only.

After receiving the temperature values, the process begins calculating the temperatures between the temperature sensors 26. To that end, the process uses conventional interpolation techniques to interpolate the temperature values in a manner that produces a thermogram as noted above (step 802). Accordingly, for a thermogram of a planar thermodynamic system at steady state, the process may be considered to increase the spatial resolution of the data.

Among other ways, some embodiments may use Laplace interpolation between the temperatures observed at each temperature sensor 26. Laplace interpolation is appropriate for this function given its physical relevance—the heat equation should simplify to the Laplace equation under the assumption of steady state. The interpolant may be constructed by applying a second-order discrete finite difference Laplacian operator to the data, imposing equality conditions on the known temperatures at the sensors 26, and solving the resulting sparse linear system using an iterative solver, such as GMRES.

FIG. 9B schematically shows one example of the thermogram at this stage of the process. This figure should be contrasted with FIG. 9A, which shows a more discrete illustration of the soles of the feet 10. At this point, the process is considered to have formed the thermogram. For effective use, however, it nevertheless still may require further processing, which was discussed above with regard to the more discrete version of the temperature map.

Step 804 therefore orients the data/thermogram to a standard coordinate system as discussed above. FIG. 9C schematically shows one example of how this step may reorient the thermogram of FIG. 9B.

Figure 9D:
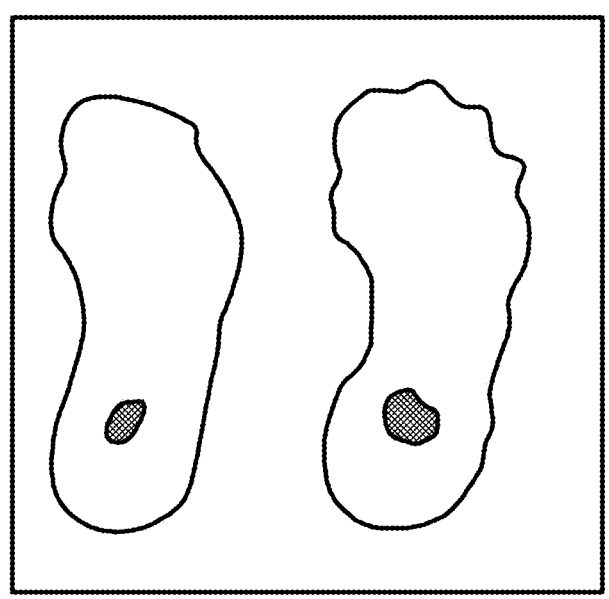

The process may end at this point, or continue to step 806, to better contrast warmer portions of the foot 10 against other portions of the foot 10 (non-thermogram embodiments also may perform this step). FIG. 9D schematically shows a thermogram produced in this manner from the thermogram of FIG. 9C. This figure more clearly shows two hotspots on the foot 10 than FIG. 9C. To that end, the process determines the baseline or normal temperature of the foot 10 for each location within some tolerance range. The amount to which the actual temperature of a portion of the foot 10 deviates from the baseline temperature of that portion of the foot 10 therefore is used to more readily show hotspots.

For example, if the deviation is negative, the thermogram may have some shade of blue, with a visual scale of faint blues being smaller deviations and richer blues being larger deviations. In a similar manner, positive deviations may be represented by some shade of red, with a visual scale of faint red being smaller deviations and richer reds being larger deviations. Accordingly, in this example, bright red portions of the thermogram readily show hotspots that may require immediate attention. Of course, other embodiments may use other colors or techniques for showing hotspots. Discussion of color coding or specific colors thus is not intended to limit all embodiments.

Similar processes may be used with non-thermogram embodiments.

Accordingly, by using a wide array of temperature sensors 26 in the confined interior 20 of a footwear product, illustrative embodiments precisely locate trouble spots that may eventually become a significant health problem. Among other benefits, this wide sensor array 26 technologically advances the state of the art by enabling a closed-platform system (i.e., footwear 16) to analyze a richer set of data for prescribed patterns indicative of foot maladies. Moreover, by just putting on a shoe or sock, a high-risk person (or any person) can determine if they have a foot ulcer 12 or pre-ulcer 14, or monitor the progression of either. In essence, this smart-footwear has the potential to significantly reduce or eliminate patient compliance problems, significantly improving the lives of countless high-risk people.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product (or in a computer process) for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium.

The medium may be either a tangible medium (e.g., optical or analog communications lines) or a medium implemented with wireless techniques (e.g., WIFI, microwave, infrared or other transmission techniques). The medium also may be a non-transient medium. The series of computer instructions can embody all or part of the functionality previously described herein with respect to the system. The processes described herein are merely exemplary and it is understood that various alternatives, mathematical equivalents, or derivations thereof fall within the scope of the present invention.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the larger network 32 (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the above discussion discloses various exemplary embodiments of the invention, it should be apparent that those skilled in the art can make various modifications that will achieve some of the advantages of the invention without departing from the true scope of the invention.

What is claimed is:

1. A footwear system comprising:
   a body having an interior for receiving a person's foot and an opening to the interior, the foot having an actual geometric shape;
   a flexible surface configured to at least in part conform to the person's foot;
   a plurality of temperature sensors associated with the interior of the body, the plurality of temperature sensors being configured to generate, at regular time intervals, a plurality of sets of discrete temperature data values across the geometry of the foot;
   a temperature map generator operatively coupled with the plurality of temperature sensors, the temperature map generator being configured to form a plurality of pixelated temperature maps from the sets of discrete temperature data values, each of the temperature maps comprising the discrete temperature data values at a given time based on the regular time intervals, the plurality of temperature maps forming a time series of temperature maps, each temperature map representing the actual geometric shape of at least a portion of the foot, each temperature map also including a distribution of temperatures of the at least a portion of the foot, each temperature map having a geography and each temperature map having a discontinuous temperature distribution across the geography;
   a pattern recognition system operatively coupled with the temperature map generator, the pattern recognition system being configured to determine when the time series of temperature maps presents at least one of a plurality of prescribed patterns, the pattern recognition system configured to compare at least two of the plurality of discrete temperature data values from each temperature map and produced by the sensors to determine when the temperature map presents at least one of the plurality of prescribed patterns; and
   an analyzer operatively coupled with the pattern recognition system, the analyzer being configured to produce output information indicating an emergence of an ulcer or a pre-ulcer on a portion on the foot, the analyzer being configured to produce the output information as a function of when the time series of temperature maps is determined to present the at least one of the plurality of prescribed patterns.

2. The footwear system as defined by claim 1 further comprising an interface to communicate with one or more remote devices, further wherein at least one of the temperature map generator, pattern recognition system, and analyzer is remote from the body, the temperature sensors communicating with the at least one of the temperature map generator, pattern recognition system and analyzer using the interface.

3. The footwear system as defined by claim 1 wherein at least one of the temperature map generator, pattern recognition system and, analyzer are integrated into the body.

4. The footwear system as defined by claim 1 wherein the temperature map generator is configured to form a geometrically accurate outline of at least a portion of the foot based on the plurality of discrete temperature data values.

5. The footwear system as defined by claim 1 wherein the analyzer is configured to determine, using the time series of temperature maps, a region of the foot that presents at least one of the plurality of patterns.

6. The footwear system as defined by claim 1 wherein each temperature map is configured to form a geometric shape reflecting the actual geometric shape of at least a portion of the foot of the person based on the plurality of discrete temperature data values ("foot geometry").

7. The footwear system as defined by claim 6 where each temperature map is configured to generate the distribution of temperatures over at least a part of the foot geometry.

8. The footwear system as defined by claim 1 wherein each temperature map comprises:
   a two dimensional representation of the sole of the foot;
   wherein the two dimensional representation includes a plurality of the discrete temperature data values, the two dimensional representation not having temperature information for regions of the foot between temperature sensors.

9. The footwear system as defined by claim 1 wherein the footwear comprises a sock body.

10. The footwear system as defined by claim 1 wherein the body comprises a shoe body, a sneaker body, or a slipper body.

11. The footwear system as defined by claim 1 wherein the body comprises an insole at least in part supporting the plurality of temperature sensors.

12. A footwear system comprising:
    an insole for receiving a person's foot and configured to be positioned within the interior of a closed platform, the foot having an actual geometric shape;
    a plurality of temperature sensors in communication with a top surface of the insole, the plurality of temperature sensors being configured to generate, at regular time intervals, a plurality of discrete temperature data values across the geometry of the foot;
    a temperature map generator operatively coupled with the plurality of temperature sensors, the temperature map generator being configured to form a pixelated temperature map from the plurality of discrete temperature data values to comprise the plurality of discrete temperature data values, the temperature map representing the actual geometric shape of at least a portion of the foot, the temperature map also including a distribution of temperatures of the at least a portion of the foot, the temperature map having a geography, the temperature map having a discontinuous temperature distribution across the geography;

a pattern recognition system operatively coupled with the temperature map generator, the pattern recognition system being configured to determine when the temperature map having the discontinuous temperature distribution across the geography presents at least one of a plurality of prescribed patterns, the pattern recognition system configured to compare at least two of the plurality of discrete temperature data values produced by the sensors and in the temperature map to determine when the temperature map presents at least one of the plurality of prescribed patterns; and an analyzer operatively coupled with the pattern recognition system, the analyzer being configured to produce output information indicating an emergence of an ulcer or a pre-ulcer on a portion on the foot, the analyzer being configured to produce the output information as a function of when the temperature map having the discontinuous temperature distribution across the geography is determined to present the at least one of the plurality of prescribed patterns.

13. The footwear system as defined by claim 12 wherein the top surface of the insole comprises a flexible surface configured to flex to conform to the shape of at least a portion of the foot.

14. The footwear system as defined by claim 12 further comprising a closed platform with a body having an interior configured to receive the insole.

15. The footwear system as defined by claim 12 wherein at least one of the temperature map generator, pattern recognition system, and analyzer are integrated into the closed platform.

16. The footwear system as defined by claim 12 wherein the temperature map generator is configured to form a geometrically accurate outline of at least a portion of the foot based on the plurality of discrete temperature data values.

17. The footwear system as defined by claim 12 wherein the analyzer is configured to determine, using the temperature map, a region of the foot that presents at least one of the plurality of patterns.

18. The footwear system as defined by claim 12 wherein the temperature map is configured to form a geometric shape reflecting the actual geometric shape of at least a portion of the foot of the person based on the plurality of discrete temperature data values ("foot geometry").

19. The footwear system as defined by claim 18 where the temperature map is configured to generate the distribution of temperatures over at least a part of the foot geometry.

20. The footwear system as defined by claim 12 wherein the temperature map comprises:

a two dimensional representation of the sole of the foot;

wherein the two dimensional representation includes a plurality of the discrete temperature data values, the two dimensional representation not having temperature information for regions of the foot between temperature sensors.

21. The footwear system as defined by claim 1 wherein the plurality of temperature sensors are on a substrate within the interior of the body, further wherein the plurality of temperature sensors comprises a first contact temperature sensor and a second contact temperature sensor, the first contact temperature sensor being adjacent to the second contact temperature sensor on the substrate, the first contact temperature sensor being conductively thermally isolated from the second contact temperature sensor within the interior of the body.

22. The footwear system as defined by claim 1 wherein the pattern recognition system is configured to determine when the time series of temperature maps presents at least one of a plurality of prescribed patterns by using up to all of the plurality of temperature sensors forming the temperature map.

23. The footwear system as defined by claim 1 wherein the plurality of temperature sensors are on a substrate within the interior of the body, the substrate having an outer periphery with a non-rectangular shape.

24. The footwear system as defined by claim 23 wherein the outer periphery has a concave portion and a convex portion.

25. The footwear system as defined by claim 24 wherein the body is formed to be a shoe body, a sneaker body, or a slipper body, the interior having a contoured interior surface having an arch support, the plurality of temperature sensors being on a substrate that is shaped to conform to the arch support of the interior surface.

26. The footwear system as defined by claim 25 wherein the interior has a rechargeable battery to energize the plurality of temperature sensors, the interior also having a pocket configured to contain the rechargeable battery.

27. The footwear system as defined by claim 1 wherein the interior of the body comprises a confined interior, the body, confined interior, and opening configured such that a received foot is snugly positioned within the confined interior.

28. The footwear system as defined by claim 1 wherein the plurality of temperature sensors are on a substrate and fitted within the interior of the body.

* * * * *